(12) United States Patent
Yamaya et al.

(10) Patent No.: US 10,234,570 B2
(45) Date of Patent: Mar. 19, 2019

(54) PET DEVICE, PET-MRI APPARATUS, AND IMAGE PROCESSING METHOD

(71) Applicants: Toshiba Medical Systems Corporation, Otawara-shi (JP); National Institutes for Quantum and Radiological Science and Technology, Chiba-shi (JP)

(72) Inventors: Taiga Yamaya, Chiba (JP); Takayuki Obata, Chiba (JP); Iwao Kanno, Chiba (JP); Takuzo Takayama, Tochigi (JP); Hitoshi Yamagata, Tochigi (JP); Kazuya Okamoto, Saitama (JP)

(73) Assignees: Toshiba Medical Systems Corporation, Otawara-shi (JP); National Institutes for Quantum and Radiological Science and Technology, Chiba-shi (JP)

( * ) Notice: Subject to any disclaimer, the term of this patent is extended or adjusted under 35 U.S.C. 154(b) by 0 days.

(21) Appl. No.: 13/938,592

(22) Filed: Jul. 10, 2013

(65) Prior Publication Data
US 2013/0324836 A1   Dec. 5, 2013

Related U.S. Application Data

(63) Continuation of application No. PCT/JP2012/050400, filed on Jan. 11, 2012.

(30) Foreign Application Priority Data

Jan. 11, 2011 (JP) ................................. 2011-003413

(51) Int. Cl.
*G01T 1/164* (2006.01)
*A61B 6/03* (2006.01)
(Continued)

(52) U.S. Cl.
CPC .............. *G01T 1/164* (2013.01); *A61B 6/037* (2013.01); *G01R 33/481* (2013.01);
(Continued)

(58) Field of Classification Search
None
See application file for complete search history.

(56) References Cited

U.S. PATENT DOCUMENTS 6,346,706 B1*  2/2002 Rogers et al. ........... 250/363.04
2002/0195565 A1* 12/2002 Lecoq ...................... 250/363.03
(Continued)

FOREIGN PATENT DOCUMENTS

CN         1760694 A      4/2006
CN         1919147 A      2/2007
(Continued)

OTHER PUBLICATIONS

Rafecas, M., et al. "Inter-crystal scatter in a dual layer, high resolution LSO-APD positron emission tomograph." Physics in medicine and biology 48.7 (2003): 821.*
(Continued)

*Primary Examiner* — Carolyn Pehlke
(74) *Attorney, Agent, or Firm* — Oblon, McClelland, Maier & Neustadt, L.L.P.

(57) ABSTRACT

In a PET device, a first detector includes a plurality of first scintillators and detects gamma rays emitted from positron-emitting radionuclides injected into a subject. A second detector is provided on the outer circumferential side of the first detector, includes a plurality of second scintillators arranged in an arrangement surface density lower than that of the first scintillators, and detects gamma rays that have passed through the first detector. A counted information acquiring unit acquires, as first counted information and second counted information, the detection positions, energy values, and detection time regarding gamma rays detected by the first detector and the second detector. Based on the detection time contained in each of the first counted information and the second counted information, an energy value adder generate corrected counted information by summing
(Continued)

the energy values contained in the first counted information and the second counted information.

14 Claims, 13 Drawing Sheets

(51) Int. Cl.
*A61B 6/00* (2006.01)
*G01T 1/29* (2006.01)
*G01R 33/48* (2006.01)

(52) U.S. Cl.
CPC ........ *G01R 33/4808* (2013.01); *G01T 1/2985* (2013.01); *A61B 6/4417* (2013.01); *A61B 6/5229* (2013.01)

(56) References Cited

U.S. PATENT DOCUMENTS

| | | | |
|---|---|---|---|
| 2004/0195512 A1* | 10/2004 | Crosetto | 250/363.04 |
| 2007/0102641 A1 | 5/2007 | Schmand et al. | |
| 2008/0284428 A1* | 11/2008 | Fiedler et al. | 324/307 |
| 2009/0121141 A1* | 5/2009 | Eriksson et al. | 250/363.04 |
| 2011/0001049 A1 | 1/2011 | Shibuya et al. | |
| 2011/0272587 A1* | 11/2011 | Siegel | G01T 1/1644 250/362 |
| 2011/0297840 A1* | 12/2011 | Tanaka et al. | 250/393 |

FOREIGN PATENT DOCUMENTS

| | | |
|---|---|---|
| CN | 101238392 A | 8/2008 |
| EP | 1 316 818 A2 | 6/2003 |
| JP | 2005-114367 A | 4/2005 |
| JP | 2008-525161 A | 7/2008 |
| WO | 2009-125480 A1 | 10/2009 |

OTHER PUBLICATIONS

Yamaya, Taiga, et al. "A proposal of an open PET geometry." Physics in medicine and biology 53.3 (2008): 757.*
Yamaya, Taiga, et al. "Imaging simulations of an "OpenPET" geometry with shifting detector rings." Radiological physics and technology 2.1 (2009): 62-69.*
Lewellen, Tom K. "Recent developments in PET detector technology." Physics in medicine and biology 53.17 (2008): R287.*
McElroy, David P., et al. "First results from MADPET-II: a novel detector and readout system for high resolution small animal PET." Nuclear Science Symposium Conference Record, 2003 IEEE. vol. 3. IEEE, 2003.*
Combined Office Action and Search Report dated Jan. 28, 2014 in Chinese Patent Application No. 201280000378.0 (with English Translation of Category of Cited Documents).
International Search Report dated Apr. 10, 2012 for PCT/JP2012/050400 filed Jan. 11, 2012 with English Translation.
International Written Opinion dated Apr. 10, 2012 for PCT/JP2012/050400 filed Jan. 11, 2012.

* cited by examiner

| MODULE ID | P | E | T |
|---|---|---|---|
| | P111 | E111 | T111 |
| | P112 | E112 | T112 |
| D11 | P113 | E113 | T113 |
| | . | . | . |
| | . | . | . |
| | . | . | . |

| MODULE ID | P | E | T |
|---|---|---|---|
| | P121 | E121 | T121 |
| | P122 | E122 | T122 |
| D12 | P123 | E123 | T123 |
| | . | . | . |
| | . | . | . |
| | . | . | . |

| MODULE ID | P | E | T |
|---|---|---|---|
| | P131 | E131 | T131 |
| | P132 | E132 | T132 |
| D13 | P133 | E133 | T133 |
| | . | . | . |
| | . | . | . |
| | . | . | . |

| MODULE ID | P | E | T |
|---|---|---|---|
| D21 | P211 | E211 | T211 |
| | P212 | E212 | T212 |
| | P213 | E213 | T213 |
| | ⋮ | ⋮ | ⋮ |

| MODULE ID | P | E | T |
|---|---|---|---|
| D22 | P221 | E221 | T221 |
| | P222 | E222 | T222 |
| | P223 | E223 | T223 |
| | ⋮ | ⋮ | ⋮ |

| MODULE ID | P | E | T |
|---|---|---|---|
| D23 | P231 | E231 | T231 |
| | P232 | E232 | T232 |
| | P233 | E233 | T233 |
| | ⋮ | ⋮ | ⋮ |

| P | E | T |
|---|---|---|
| P111 | E111+E211 | T111 |
| P112 | E112+E212 | T112 |
| P113 | E113+E213 | T113 |
| ⋮ | ⋮ | ⋮ |
| P131 | E131+E231 | T131 |
| P132 | E132+E232 | T132 |
| P133 | E133+E233 | T133 |
| ⋮ | ⋮ | ⋮ |
| P151 | E151+E221 | T151 |
| P152 | E152+E222 | T152 |
| P153 | E153+E223 | T153 |
| ⋮ | ⋮ | ⋮ |

| P111 | E111+E211 | T111 | P151 | E151+E221 | T151 |
|------|-----------|------|------|-----------|------|
| P112 | E112+E212 | T112 | P132 | E132+E232 | T132 |
| P113 | E113+E213 | T113 | P133 | E133+E233 | T133 |
| . | . | . | . | . | . |
| . | . | . | . | . | . |
| . | . | . | . | . | . |

FIG.8

| P | E | T |
|---|---|---|
| P241 | E241+E161 | T241 |
| ⋮ | ⋮ | ⋮ |
| P251 | E251+E181 | T251 |
| ⋮ | ⋮ | ⋮ |
| P261 | E261+E191 | T261 |
| ⋮ | ⋮ | ⋮ |

FIG.9

| P | E | T |
|---|---|---|
| P111 | E111+E211 | T111 |
| P112 | E112 | T112 |
| P113 | E113+E213 | T113 |
| ⋮ | ⋮ | ⋮ |
| P131 | E131 | T131 |
| P132 | E132+E232 | T132 |
| P133 | E133+E233 | T133 |
| ⋮ | ⋮ | ⋮ |
| P151 | E151+E221 | T151 |
| P152 | E152+E222 | T152 |
| ⋮ | ⋮ | ⋮ |

FIG.10

| P | E | T |
|---|---|---|
| P241 | E241+E161 | T241 |
| P242 | E242 | T242 |
| ⋮ | ⋮ | ⋮ |
| P251 | E251+E181 | T251 |
| P252 | E252 | T252 |
| ⋮ | ⋮ | ⋮ |
| P261 | E261+E191 | T261 |
| ⋮ | ⋮ | ⋮ |

FIG.14

| MODULE ID | P | E | T |
|---|---|---|---|
| D31 | P311 | E311 | T311 |
|  | P312 | E312 | T312 |
|  | P313 | E313 | T313 |
|  | ... | ... | ... |

| MODULE ID | P | E | T |
|---|---|---|---|
| D32 | P321 | E321 | T321 |
|  | P322 | E322 | T322 |
|  | P323 | E323 | T323 |
|  | ... | ... | ... |

| MODULE ID | P | E | T |
|---|---|---|---|
| D33 | P331 | E331 | T331 |
|  | P332 | E332 | T332 |
|  | P333 | E333 | T333 |
|  | ... | ... | ... |

| MODULE ID | P | E | T |
|---|---|---|---|
| D41 | P411 | E411 | T411 |
|  | P412 | E412 | T412 |
|  | P413 | E413 | T413 |
|  | ... | ... | ... |

| MODULE ID | P | E | T |
|---|---|---|---|
| D42 | P421 | E421 | T421 |
|  | P422 | E422 | T422 |
|  | P423 | E423 | T423 |
|  | ... | ... | ... |

| MODULE ID | P | E | T |
|---|---|---|---|
| D43 | P431 | E431 | T431 |
|  | P432 | E432 | T432 |
|  | P433 | E433 | T433 |
|  | ... | ... | ... |

| P | E | T |
|---|---|---|
| P111 | E111+E211 | T111 |
| P112 | E112+E212 | T112 |
| P113 | E113+E213 | T113 |
| ⋮ | ⋮ | ⋮ |
| P151 | E151+E221 | T151 |
| P152 | E152+E222 | T152 |
| P153 | E153+E223 | T153 |
| ⋮ | ⋮ | ⋮ |

FIG.17

| P | E | T |
|---|---|---|
| P311 | E311+E411 | T311 |
| P312 | E312+E412 | T312 |
| P313 | E313+E413 | T313 |
| ⋮ | ⋮ | ⋮ |
| P351 | E351+E421 | T351 |
| P352 | E352+E422 | T352 |
| P353 | E353+E423 | T353 |
| ⋮ | ⋮ | ⋮ |

| P111 | E111+E211 | T111 | P151 | E151+E221 | T151 | HIGH RESOLUTION | |
| --- | --- | --- | --- | --- | --- | --- | --- |
| P311 | E311+E411 | T311 | P351 | E351+E421 | T351 | HIGH RESOLUTION | |
| P152 | E152+E222 | T152 | P352 | E352+E422 | T352 | HIGH RESOLUTION | SIMULTANEOUS IMAGING |
| P112 | E112+E212 | T112 | P412 | E412 | T412 | | SIMULTANEOUS IMAGING |
| P312 | E312+E412 | T312 | P212 | E212 | T212 | | SIMULTANEOUS IMAGING |
| ⋮ | ⋮ | ⋮ | ⋮ | ⋮ | ⋮ | ⋮ | ⋮ |

US 10,234,570 B2

PET DEVICE, PET-MRI APPARATUS, AND IMAGE PROCESSING METHOD

CROSS-REFERENCE TO RELATED APPLICATIONS

This application is a continuation of PCT international application Ser. No. PCT/JP2012/050400 filed on Jan. 11, 2012 which designates the United States, and which claims the benefit of priority from Japanese Patent Application No. 2011-003413, filed on Jan. 11, 2011; the entire contents of which are incorporated herein by reference.

FIELD

Embodiments described herein relate to a Positron Emission Tomography (PET) device, a Positron Emission Tomography—Magnetic Resonance Imaging (PET-MRI) apparatus, and an image processing method.

BACKGROUND

Conventional positron emission computed tomography (PET) devices are known that generate a PET image representing the distribution in a subject of an agent that is labeled with positron-emitting radionuclides. A PET device generally includes a ring-shaped PET detector that is arranged so as to enclose a subject. The PET detector is formed, for example, by arranging, in a ring, multiple detector modules including scintillators that convert gamma rays (including annihilation radiation) into visible light. For PET devices, there may be a requirement to reduce the cost of manufacturing the PET detectors and, for example, to reduce the thickness of the scintillators of the PET detectors in order to improve TOF (time of flight) temporal resolution.

In conventional PET devices, however, when the thickness of the scintillators of the PET detector is reduced, the possibility increases of gamma rays passing without being detected by the PET detector, which may decrease the image quality of a captured PET image.

BRIEF DESCRIPTION OF THE DRAWINGS

FIG. 4 includes tables of exemplary second counted information stored in the counted information storage unit according to the first embodiment.

FIG. 5 is a table of exemplary corrected counted information generated by an energy value adder according to the first embodiment.

FIG. 8 is a table (1) of other corrected counted information generated by the energy value adder according to the first embodiment.

FIG. 9 is a table (2) of still other exemplary corrected counted information generated by the energy value adder according to the first embodiment.

FIG. 10 is a table (3) of still other exemplary corrected counted information generated by the energy value adder according to the first embodiment.

FIG. 14 includes tables of exemplary third counted information stored in a counted information storage unit according to the second embodiment.

FIG. 15 includes tables of exemplary fourth counted information stored in the counted information storage unit according to the second embodiment.

FIG. 16 is a table of exemplary first corrected counted information generated by an energy value adder according to the second embodiment.

FIG. 17 is a table of exemplary second corrected counted information generated by the energy value adder according to the second embodiment.

DETAILED DESCRIPTION

A PET device comprising according to an embodiment includes a first detector, a second detector, a counted information acquiring unit, an energy value adder, a simultaneous counted information generator, and an image reconstruction unit. The first detector has a ring shape, includes a plurality of first scintillators, and detects gamma rays emitted from positron-emitting radionuclides injected into a subject. The second detector has a ring shape, includes a plurality of second scintillators arranged in an arrangement surface density lower than that of the first scintillators, is provided on the outer circumferential side of the first detector, and detects gamma rays that have passed through the first detector. A counted information acquiring unit acquires, as first counted information, a detection position, an energy value, and a detection time regarding the gamma ray detected by the first detector and acquires, as second counted information, a detection position, an energy value, and a detection time regarding the gamma ray detected by the second detector. An energy value adder, based on the detection time contained in the first counted information and the detection time contained in the second counted information, generates corrected counted information by adding the energy value contained in the second counted information to the energy value contained in the first counted information. A simultaneous counted information generator, based on the corrected counted information generated by the energy value adder, generates, as simultaneous counted information, a combination of corrected counted information on simultaneous detection of gamma rays emitted from the positron-emitting radionuclide. An image reconstruction unit reconstructs a PET image in accordance with the simultaneous counted information generated by the simultaneous counted information generator.

A PET device, a PET-MRI apparatus, and an image processing method according to embodiments will be described in detail below with reference to the drawings.

First Embodiment

Figure 1:
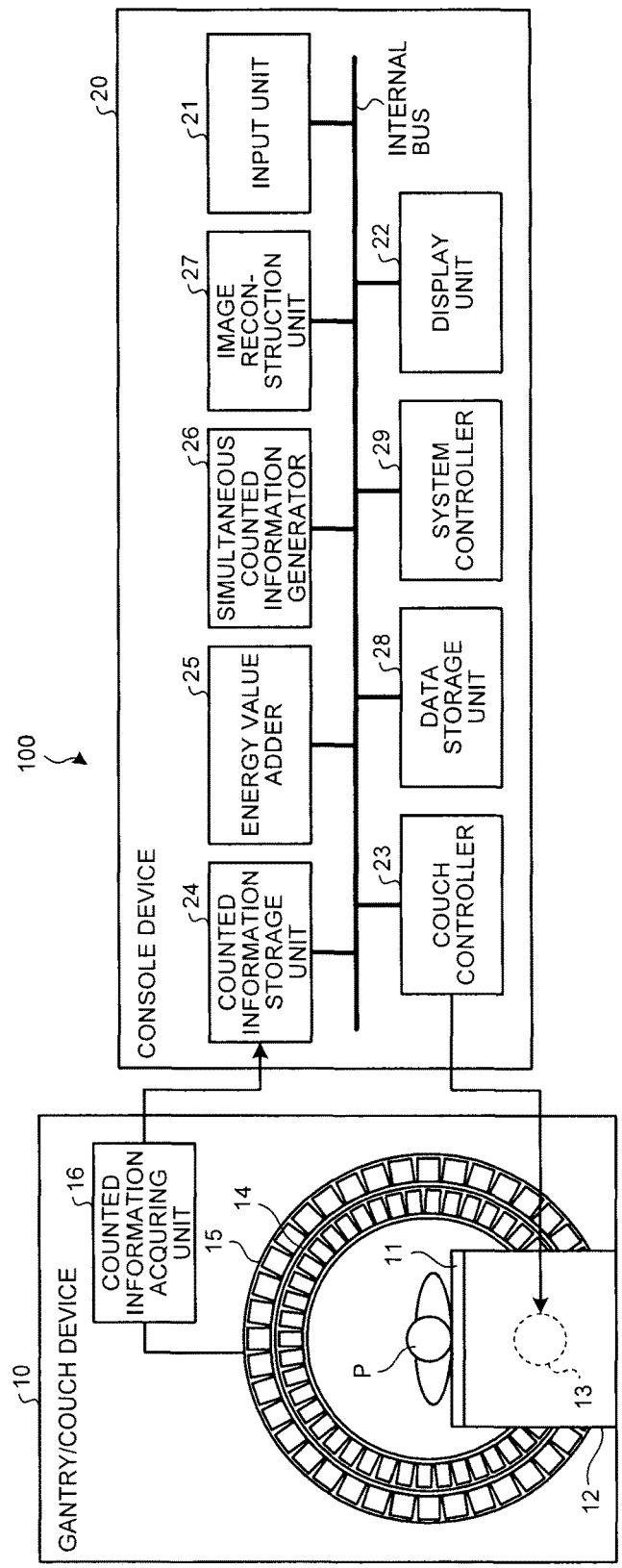
FIG. 1 is a diagram of a configuration of a PET device according to a first embodiment.

First, an embodiment of a PET device will be described as a first embodiment. FIG. 1 is a diagram of a configuration of a PET device 100 according to the first embodiment. As depicted in FIG. 1, the PET device 100 includes a gantry/couch device 10 and a console device 20.

The gantry/couch device 10 counts, in a monitoring period, pairs of gamma rays that are emitted from positron-emitting radionuclides that are injected into a subject P and selectively taken into the living tissue of the subject P. For example, the gantry/couch device 10 includes a couchtop 11, a couch 12, a couch driver 13, PET detectors 14 and 15, and a counted information acquiring unit 16. As depicted in FIG. 1, the gantry/couch device 10 has a hollow space serving as an imaging inlet.

The couchtop 11 is a bed on which the subject P lies and the couchtop 11 is arranged on the couch 12. The couch driver 13 moves the subject P into the imaging inlet of the gantry/couch device 10 by moving the couch 12 under the control of a couch controller 23, which will be described below.

The PET detector 14 is formed in a ring and detects gamma rays that are emitted from the positron-emitting radionuclides that are injected into the subject P. The PET detector 15 is formed in a ring and provided on the outer circumferential side of the PET detector 14. The PET detector 15 detects the gamma rays that have passed through the PET detector 14. The PET detectors 14 and 15 are formed by arranging, in a ring, multiple detector modules and are normally provided in layers in the depth direction in FIG. 1.

Each detector module that forms the PET detectors 14 and 15 is a photon counting detector that detects gamma rays emitted from the subject P. For example, each detector module includes scintillators and a photomultiplier tubes (PMT) and may further include a light guide. The scintillator is formed by two-dimensionally arraying NaI (sodium Iodine), BGO (Bismuth Germanate), LYSO (Lutetium Yttrium Oxyorthosilicate), LSO (Lutetium Oxyorthosilicate), or LGSO (Lutetium Oxyorthosilicate) that converts a gamma ray emitted from the subject P and incident on the scintillator into visible light. Multiple photomultiplier tubes are densely arranged via a light guide, multiply the visible light emitted from the scintillator, and convert the visible light into an electric signal. The light guide is formed from a plastic material or a glass material that has a high transmittance and transmits the visible light output from the scintillator to the photomultiplier tubes.

The photomultiplier tube includes a photocathode that receives scintillation light and generates photoelectrons; a multistage dynode that provides an electric field that accelerates the generated photoelectrons; and an anode that is an outlet for the photoelectrons. The photoelectrons that are emitted from the photocathode because of the photoelectric effect are accelerated toward the dynode and collide with the surface of the dynode, which produces multiple electrons. This phenomenon is repeated over the multistage dynode, thereby multiplying the number of electrons, somewhat analogous to an avalanche, so that the number of electrons at the anode reaches approximately 1 million. In this example, the photomultiplier tube has a gain factor of one million. Usually, a voltage of approximately 1000 volts is applied between the dynode and the anode for the amplification using the avalanche phenomenon.

In other words, in each detector module that forms the PET detectors 14 and 15, the scintillator converts gamma rays to visible light, the photomultiplier tube converts the converted visible light to an electric signal, and thereby each detector module counts the number of gamma rays emitted from the subject P, the position where a gamma ray is detected, energy, and timing.

The scintillators of the PET detectors are formed such that, for example, in the case of LYSO, their total thickness is 20 mm or more so as to obtain a gamma ray detection efficiency of a given value or more. For example, LYSO scintillators of the PET detectors are formed such that their total thickness is approximately 22 mm. For example, it is preferable that the thickness of the scintillator of the PET detector 14 be approximately 7 to 12 mm. It is also preferable that the thickness of the scintillator of the PET detector 15 be approximately 10 to 15 mm. Note that it is preferable that the scintillator of the PET detector 14 be thinner than the scintillator of the PET detector 15.

Figures 2, 3:
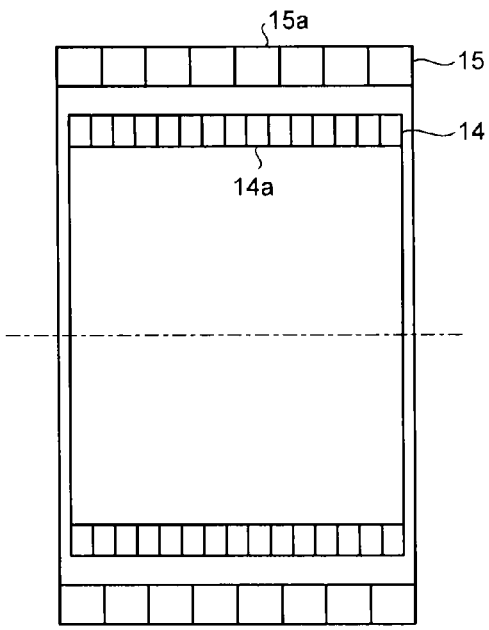
FIG. 2 is a cross-sectional view of PET detectors according to the first embodiment.
FIG. 3 includes tables of exemplary first counted information stored in a counted information storage unit according to the first embodiment.

The scintillator of the PET detector 14 is formed such that its width in the axial direction of the ring is equal to or smaller than the scintillator of the PET detector 15. FIG. 2 is a cross-sectional view of the PET detector 14 and the PET detector 15 according to the first embodiment. FIG. 2 depicts scintillators 14a of the detector modules of the PET detector 14 and scintillators 15a of the detector modules of the PET detector 15.

For example, as depicted in FIG. 2, the scintillator 14a of the PET detector 14 is formed such that its width in the axial direction of the ring is smaller than that of the scintillator 15a of the PET detector 15 and is formed such that its width in the circumferential direction viewed at the angle as depicted in FIG. 1 is also small. In other words, the PET detector 14 positioned on the inner side has a higher arrangement area density of scintillators and thus has a smaller pixel size. The PET detector 15 positioned on the outer side has a lower arrangement area density of scintillators and thus has a larger pixel size. The material of the scintillators 14a and the material of the scintillators 15a may be different from each other.

By arranging PET detectors in two layers, as described above, the probability of detecting gamma rays can be increased. Regarding the inner PET detector, by thinning the scintillators, i.e., reducing their width, and reducing the pixel size, the image quality of PET images can be increased. Regarding the outer PET detector, by increasing the pixel size, the costs of manufacturing PET detectors can be reduced.

It is preferable that, as depicted in FIG. 2, the length of the PET detector 15 in its axial direction be longer than that of the PET detector 14. Accordingly, the PET detector 15 can reliably detect scattered radiation due to gamma rays generated in the PET detector 14.

FIG. 2 depicts the case where the PET detector 14 and the PET detector 15 are arranged such that a gap is formed between the PET detectors. However, a gap is not necessarily provided between the PET detector 14 and the PET detector 15. When the gap is made small, if the ring diameter of the PET detector 15 is reduced while maintaining the thickness of the PET detector 15, the volume of the scintillators used for the PET detector 15 can be reduced while keeping the rate of detecting gamma rays and thus, manufacturing costs can be reduced. Furthermore, by increasing the ring diameter of the PET detector 15, the space in which a subject is positioned can be widened and thus a subject of a large build can be diagnosed.

In order to deal with output changes due to noise change or chronological change, calibration is regularly performed on each detector module of the PET detectors 14 and 15. The calibration includes, for example, energy calibration and time calibration. The energy calibration adjusts and balances the gain and offset of each detector module. The time calibration balances, between detector modules, the output timing of time information that is output when each detector module detects a gamma ray.

The following refers back to the description of FIG. 1. The counted information acquiring unit 16 acquires, as counted information, information based on the results of counting by the PET detectors 14 and 15. Specifically, the counted information acquiring unit 16 acquires, as first counted information, the detection position, the energy value, and the detection time regarding a gamma ray that is detected by the PET detector 14. The counted information acquiring unit 16 acquires, as second counted information, the detection, the energy value, and the detection time regarding a gamma ray that is detected by the PET detector 15. The counted information acquiring unit 16 acquires counted information with respect to each detector module of the PET detectors 14 and 15 and transmits the acquired counted information to the console device 20, which will be described below.

The counted information acquiring unit 16 performs an Anger type position calculation process in order to acquire the position of a detection scintillator in accordance with the result of counting by each detector module. Alternatively, in the counted information acquiring unit 16, when the photomultiplier tube of the detector module is a position detection photomultiplier tube, the detection scintillator and the light emitting position in the detection scintillator are acquired in the position detection photomultiplier tube. In this case, the counted information acquiring unit 16 determines a scintillator number (P) representing the position of a scintillator on which a gamma ray is incident by computing the position of each photomultiplier tube, which has converted scintillation light to an electric signal in the same detection interval and has output the electric signal, and computing the position of the center of gravity from the intensity of the electric signal. The counted information acquiring unit 16 determines a total energy value (E) of gamma rays incident on the detector module by summing the intensity of the electric signals that are output by the respective photomultiplier tubes. The counted information acquiring unit 16 also acquires the detection time (T) in which the detector module detects the gamma ray.

The detection time (T) may be an absolute time or a relative time from the time when the image capturing is started. The time may be the clock time or the number of counts of the counter. In either case, the counted information acquiring unit 16 acquires the detection time (T) with the accuracy of $10^{-12}$ seconds (psec). Through such processes, the counted information acquiring unit 16 acquires, as counted information, "P: scintillator number", "E: energy value", and "T: detection time" that are associated with "module ID".

Once the console device 20 receives an operation of the operator on the PET device, the console device 20 reconstructs a PET image in accordance with the counted information, which is acquired by the gantry/couch device 10. For example, the console device 20 includes an input unit 21, a display unit 22, the couch controller 23, a counted information storage unit 24, an energy value adder 25, a simultaneous counted information generator 26, an image reconstruction unit 27, a data storage unit 28, and a system controller 29. The units of the console device 20 are connected via an internal bus.

The input unit 21 includes a mouse and a keyboard that are used by the operator of the PET device to input various instructions and various settings and transfers, to the system controller 29, the information on instructions and settings received from the operator. For example, the input unit 21 receives, from the operator, a reconstruction condition for reconstructing a PET image and a correction condition for image correction.

The display unit 22 is a monitor referred to by the operator and, under the control of the system controller 29, displays a PET image to the operator and displays a GUI (graphical user interface) to receive various instructions and various settings from the operator via the input unit 21.

The couch controller 23 moves the subject P into the imaging port of the gantry/couch device 10 by controlling the couch driver 13.

The counted information storage unit 24 stores the first counted information and the second counted information of each detector module that are acquired by the counted information acquiring unit 16. FIG. 3 includes tables of exemplary first counted information stored in the counted information storage unit 24 according to the first embodiment. FIG. 4 includes tables of exemplary second counted information stored in the counted information storage unit 24 according to the first embodiment. In FIGS. 3 and 4, "P", "E", and "T" denote "scintillator number", "energy value", and "detection time", respectively.

For example, as shown in FIG. 3, the counted information storage unit 24 stores "P:P111, E:E111, T:T111" and "P:P112, E:E112, T:T112" as first counted information acquired in accordance with the results of counting performed by the detector module of "module ID:D11" of the PET detector 14. The counted information storage unit 24 similarly stores first counted information acquired in accordance with the results of counting performed by the detector modules of "module ID:D12" and "module ID:D13" of the PET detector 14.

For example, as shown in FIG. 4, the counted information storage unit 24 stores "P:P211, E:E211, T:T211" and "P:P212, E:E212, T:T212" as second counted information acquired in accordance with the results of counting performed by the detector module of "module ID:D21" of the PET detector 15. The counted information storage unit 24 similarly stores second counted information acquired in accordance with the results of counting performed by the detector modules of "module ID:D22" and "module ID:D23" of the PET detector 15.

The following refers back to the description of FIG. 1. On the basis of the detection time contained in the first counted information and the detection time contained in the second counted information, the energy value adder 25 adds the energy value contained in the second counted information to the energy value contained in the first calculated information and generates corrected counted information.

For example, on the basis of a vicinity condition that is input by the operator via the input unit 21, the energy value adder 25 searches for the PET detector 15 that satisfies the vicinity condition on the PET detector 14. The vicinity condition defines, for example, five scintillators in total including two scintillators on each of both sides of the scintillator of the PET detector 15 right outside the scintillator of the PET detector 14 that has detected scintillation light.

Specifically, the energy value adder 25 generates corrected counted information on the basis of a time window width contained in the reconstruction condition input by the operator via the input unit 21. The value of the window value is specified as, for example, 600 psec, which is the temporal resolution (FWHM) of the detector, etc. For example, the energy value adder 25 refers to the first counted information shown in FIG. 3 and the second counted information shown in FIG. 4 and searches for a combination of first counted information and second counted information where the difference of the detection time (T) is within the "time window width: 600 psec", which is a combination that satisfies the vicinity condition.

Because gamma rays are emitted in approximately opposite directions when a positron emitted from the agent interacts with an electron and they annihilate each other, with the single occurrence of gamma rays, the gamma rays interact with two scintillators of the PET detector 14, so that the first counted information is highly likely to contain two sets of information. If the first counted information contains two sets of information, the information is acquired from the detector modules directly opposite each other.

In contrast, the second counted information is highly likely to contain information on the gamma rays, which are scattered when the gamma rays generated by the single annihilation, pass through the scintillators of the PET detector 14. By using the window width condition of 600 psec and the vicinity condition, the information paired with the gamma ray that flew in one direction from the annihilation position and interacted can be chosen from the first counted information and the second counted information.

Regarding the time window, a time window of a width of 600 psec may be generated according to a reference clock when occurrence of the first counted information of the PET detector 14 is observed. Alternatively, for example, time windows of 200 psec may be generated successively and four time windows containing a latter three time windows starting from the time when the occurrence of the first counted information is observed may be regarded as one window. In this case, the time window width may be between 600 psec and 800 psec.

With respect to each window acquired by the searching, the energy value adder 25 generates corrected counted information by adding the energy value contained in the second counted information to the energy value contained in the first counted information. On the basis of the corrected counted information obtained by the adding, the energy value adder 25 compares the energy value contained in the corrected counted information and the energy value of the gamma ray emitted from the positron-emitting radionuclide and leaves, as chosen data, only the corrected counted information where the difference between the energy values is within a predetermined range. The energy value adder 25 then stores the thus extracted corrected measured information in the data storage unit 28.

FIG. 5 is a table of exemplary corrected counted information generated by the energy value adder 25 according to the first embodiment. For example, as shown in FIG. 5, the energy value adder 25 generates, as corrected counted information, "P:P111, E:E111+E211, T:T111" from a combination of the first counted information "P:P111, E:E111, T:T111" shown in FIG. 3 and the second counted information "P:P211, E:E211, T:T211" shown in FIG. 4. Similarly, for example, the energy value adder 25 also generates "P:P112, E:E112+E212, T:T112" and "P:P113, E:E113+E213, T:T113" as corrected counted information.

In addition, for example, the energy value adder 25 generates, as corrected counted information, "P:P151, E:E151+E221, T:T151" from a combination of first counted information "P:P151, E:E151, T:T151" and second counted information "P:P221, E:E221, T:T221". Similarly, for example, the energy value adder 25 also generates "P:P152, E:E152+E222, T:T152" and "P:P153, E:E153+E223, T:T153" as corrected counted information.

A gamma ray that has passed through one scintillator of the PET detector 14 may be detected by multiple scintillators of the PET detector 15 because of scattering, etc. In such a case, on the basis of the time window width and the vicinity condition, the energy value adder 25 searches for a combination to be paired of first counted information and second counted information, so that combinations of single first counted information and multiple different sets of second count information is searched. In such a case, the energy value adder 25 generates corrected counted information by adding the energy value contained in each set of second counted information to the energy value contained in the first counted information.

It is assumed that, for example, regarding the first counted information "P:P112, E:E112, T:T112", a combination with the second counted information "P:P211, E:E211, T:T211", a combination with the second counted information "P:P212, E:E212, T:T212", and a combination with the second counted information "P:P213, E:E213, T:T213", are searched. In this case, the energy value adder 25 generates, as corrected counted information, "P:P112, E:E112+E211+E212+E213, T:T112".

As described above, the energy value adder 25 adds the energy value contained in the second counted information to the energy value contained in the first counted information, so that the energy value of the gamma ray detected by the PET detector 15 is added to the energy value of the gamma ray detected by the PET detector 14. Accordingly, the energy value can be compensated for of a gamma ray that has not been detected by the PET detector 14 and passed through the PET detector 14.

The following refers back to the description of FIG. 1. The simultaneous counted information generator 26 generates, as simultaneous counted information, a combination of corrected counted information on the approximately simultaneous detection of gamma rays emitted from a positron-emitting radionuclide. The time information used here is time information of the PET detector 14. Here, the gamma rays are a pair of gamma rays of 511 keV that are emitted in approximately opposite directions when a positron emitted from the agent interacts with an electron and they annihilate each other.

Specifically, the simultaneous counted information generator 26 generates simultaneous counted information on the basis of the time window width contained in the reconstruction condition, which is input by the operator via the input unit 21, the start of the time window width, and the energy window width. The value of the time window width, for example, 4 npsec, is specified in consideration of the temporal resolution of the detector and the size of field of view. Furthermore, for example, 350 keV to 650 keV is specified as the value of the energy window width.

For example, the simultaneous counted information generator 26 refers to the corrected counted information stored in the data storage unit 28 and searches for a combination of corrected counted information where the difference of the detection time (T) is within "time window width: 4 npsec" and the energy value (E) is within "energy window width: 350 keV to 650 keV". The simultaneous counted information generator 26 generates simultaneous counted information by associating the combination of corrected counted information, which is obtained by searching. The simultaneous counted information generator 26 then stores, in the data storage unit 28, the generated simultaneous counted information as projection data (sinogram data) or list mode data on the subject P.

Figures 6, 7:
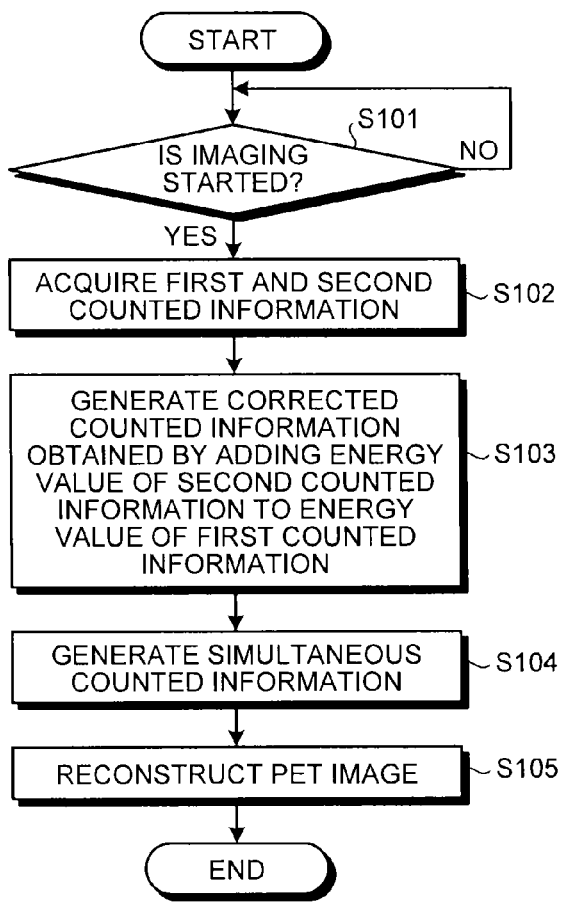
FIG. 6 is a table of exemplary simultaneous counted information generated by a simultaneous counted information generator according to the first embodiment.
FIG. 7 is a flowchart of the flow of PET image capturing performed by the PET device according to the first embodiment.

FIG. 6 is a table of exemplary simultaneous counted information generated by the simultaneous counted information generator 26 according to the first embodiment. For example, as shown in FIG. 6, the simultaneous counted information generator 26 generates a combination of the corrected counted information "P:P111, E:E111+E211, T:T111" and "P:P151, E:E151+E221, T:T151" as simultaneous counted information that is information acquired by simultaneously counting two annihilated photons. Similarly, for example, the simultaneous counted information generator 26 generates a combination of "P:P112, E:E112+E212, T:T112" and "P:P132, E:E132+E232, T:T132" and a combination of "P:P113, E:E113+E213, T:T113" and "P:P133, E:E133+E233, T:T133" as simultaneous counted information.

The operator can incorporate, in addition to the time window width and the energy window width, parameters for performing random correction to exclude accidental coincidence counting, parameters for scattering correction to exclude generation of counted information on scattered gamma rays as simultaneous counted information, parameters for sensitivity correction to correct the difference in sensitivity between each detector module, and parameters for attenuation correction to correct the energy value of a gamma ray attenuated in the subject P.

The following refers back to the description of FIG. 1. The image reconstruction unit 27 reads, as projection data, the simultaneous counted information, which is generated by the simultaneous counted information generator 26, from the data storage unit 28 and reconstructs a PET image by performing a back projection process on the read projection data. The image reconstruction unit 27 stores the reconstructed PET image in the data storage unit 28.

The system controller 29 controls the whole PET device by controlling operations of the gantry/couch device 10 and the console device 20. Specifically, the system controller 29 controls the movement of the couch 12 and a counted information acquiring process, which is performed by the counted information acquiring unit 16. Furthermore, on the basis of setting information input by the operator via the input unit 21, the system controller 29 controls the simultaneous counted information generating process, which is performed by the simultaneous counted information generator 26, and the PET image reconstructing process, which is performed by the image reconstructing unit 27. The system controller 29 controls the display unit 22 such that it displays the PET image stored in the data storage unit 28.

The flow of a PET image capturing performed by the PET device 100 according to the first embodiment will be described here. FIG. 7 is a flowchart of the flow of PET image capturing performed by the PET device 100 according to the first embodiment. As shown in FIG. 7, once the PET device 100 receives an imaging start instruction from the operator via the input unit 21 after moving the subject P into the imaging port of the gantry/couch device 10 (YES at step S101), the PET device 100 performs the following process.

First, the counted information acquiring unit 16 acquires, as first counted information, the detection position, the energy value, and the detection time regarding a gamma ray detected by the PET detector 14. The counted information acquiring unit 16 acquires, as second counted information, the gamma ray detection position, the energy value, and the detection time regarding a gamma ray detected by the PET detector 15 (step S102).

Subsequently, on the basis of the detection time contained in the first counted information and the detection time contained in the second counted information, the energy value adder 25 generates corrected counted information by adding, to the energy value contained in the first counted information, the energy value contained in the second counted information, which satisfies a vicinity condition and occurring in the same time window (step S103).

Subsequently, on the basis of the corrected counted information generated by the energy value adder 25, the simultaneous counted information generator 26 then generates, as simultaneous counted information, a combination of corrected counted information on the approximately simultaneous detection of gamma rays emitted from a positron-emitting radionuclide (step S104). The time information used here is time information of the PET detector 14.

The image reconstructing unit 27 then obtains the position where annihilated radiation occurs by a TOF technique, etc. on the basis of the simultaneous counted information, which is generated by the simultaneous counted information generator 26, and reconstructs a PET image in accordance with the assembly of a large volume of data (step S105). The reconstructed PET image is displayed on the display unit 22.

As described above, the PET device 100 according to the first embodiment includes the PET detector 14, the PET detector 15, the counted information acquiring unit 16, the energy value adder 25, the simultaneous counted information generator 26, and the image reconstruction unit 27. The PET detector 14 is formed to be ring-shaped and detects gamma rays emitted from positron-emitting radionuclides injected into the subject P. The PET detector 15 is formed to be ring-shaped, is provided on the outer circumferential side of the PET detector 14, and detects gamma rays that have passed through the PET detector 14. The counted information acquiring unit 16 acquires, as first counted information, the detection position, the energy value, and the detection time regarding a gamma ray detected by the PET detector 14 and acquires, as second counted information, the detection position, the energy value, and the detection time regarding a gamma ray detected by the PET detector 15. On the basis of the detection time contained in the first counted information and the detection time contained in the second counted information, the energy value adder 25 generates corrected counted information by adding the energy value contained in the second counted information to the energy value contained in the first counted information. On the basis of the corrected counted information generated by the energy value adder 25, the simultaneous counted information generator 26 generates, as simultaneous counted information, a combination of corrected counted information on the approximately simultaneous detection of gamma rays emitted from a positron-emitting radionuclide. The time information used here is the time information of the PET detector 14. The image reconstruction unit 27 reconstructs a PET image as projection data by using, as projection data, the simultaneous counted information generated by the simultaneous counted information generator 26. In other words, in the first embodiment, the inner PET detector 14 ensures the image quality of the PET image and the inner PET detector 15 ensures the efficiency of detecting gamma rays. Thus, according to the first embodiment, the image quality of captured PET images can be improved.

In the first embodiment, a case is described where the energy value adder 25 adds the energy value contained in the second counted information to the energy value contained in the first counted information so that the PET detector 15 compensates for the energy value of a gamma ray that the inner PET detector 14 has not detected.

However, for example, the gamma ray having passed without having been detected by the PET detector 14 may possibly be detected by the PET detector 15 first, reflected by the scintillator of the PET detector 15 and, then detected by the PET detector 14. The inner PET detector 14 may compensate for the energy value of the gamma ray that has not been detected by the outer PET detector 15.

In such a case, as described in the first embodiment, the energy value adder 25 searches for the PET detector 15 that satisfies the vicinity condition on the inner PET detector 14 and generates the "corrected counted information obtained from the inner PET detector 14" (see FIG. 5).

The energy value adder 25 further searches for the PET detector 14 that satisfies a vicinity condition on the inner PET detector 15 and generates "corrected counted information based on the outer PET detector 15". The vicinity condition on the inner PET detector 15 defines, for example, five scintillators in total including two scintillators on each of both sides of the scintillator of the PET detector 14 right outside the scintillator of the PET detector 15 that has detected scintillation light.

The energy value adder 25 here, for example, refers to the first counted information shown in FIG. 3 and the second counted information shown in FIG. 4 and searches for a combination of first counted information and second counted information where the difference of the detection time (T) is within "time window width: 600 psec", which is a combination that satisfies the vicinity condition on the PET detector 15.

The energy value adder 25 generates corrected counted information by adding the energy value contained in the first counted information to the energy value contained in the second counted information for each combination obtained by the searching. On the basis of the corrected counted information obtained by the adding, the energy value adder 25 compares the energy value contained in the corrected counted information and the energy value of the gamma ray emitted from the positron-emitting radionuclide and leaves, as chosen data, only the corrected counted information where the energy value difference is within a predetermined range. Thereafter, the energy value adder 25 stores the thus extracted corrected counted information as "corrected counted information obtained from the outer PET detector 15" in the data storage unit 28.

FIG. 8 is a table of other exemplary corrected counted information generated by the energy value adder 25 according to the first embodiment. As shown in FIG. 8, for example, the energy value adder 25 generates, as corrected counted information, "P:P241, E:E241+E161, T:T241" from a combination of second counted information "P:P241, E:E241, T:T241" and first counted information "P:P161, E:E161, T:T161". Similarly, for example, the energy value adder 25 generates, as corrected counted information, "P:P251, E:E251+E181, T:T251" and "P:P261, E:E261+E191, T:T261".

As described above, the energy value adder 25 adds the energy value contained in the first counted information to the energy value contained in the second counted information, so that the energy value of the gamma ray detected by the PET detector 14 is added to the energy value of the gamma ray detected by the PET detector 15. Accordingly, the PET detector 14 can compensate for the energy value of the gamma ray that has not been detected by the PET detector 15.

In the first embodiment, a case is described where the energy value adder 25 compares the energy value of the corrected counted information, which is obtained by adding the energy value of the first counted information to the energy value of the second counted information, with the energy value of the gamma ray emitted from the positron-emitting radionuclide and then extracts corrected counted information where the energy difference is within a predetermined range.

However, for example, the difference between the energy value of the gamma ray emitted from the positron-emitting radionuclide and only one of the energy value of the first counted information and the energy value of the second counted information may be within the predetermined range. In such a case, for example, the energy value adder 25 may use only one of the energy value of the first counted information and the energy value of the second counted information to generate corrected counted information.

FIGS. 9 and 10 are tables of other exemplary corrected counted information generated by the energy value adder 25 according to the first embodiment. As shown in FIG. 9, for example, when generating "corrected counted information based on the inner PET detector 14", if the difference between the energy value E112 and the energy value of a gamma ray emitted from a positron-emitting radionuclide is within the predetermined range in the first counted information "P:P112, E:E112, T:T112" shown n FIG. 3, the energy value adder 25 generates "P:P112, E:E112, T:T112" as corrected information. Similarly, for example, if the difference between the energy value E132 and the energy value of a gamma ray emitted from a positron-emitting radionuclide is within the predetermined range in first counted information "P:P131, E:E131, T:T131" shown in FIG. 3, the energy value adder 25 generates"P:P131, E:E131, T:T131" as corrected information by using only the energy value E132.

For example, as shown in FIG. 10, when generating "corrected counted information based on the inner PET detector 15", if the difference between the energy value E242 and the energy value of a gamma ray emitted from a positron-emitting radionuclide is within the predetermined range in the second counted information "P:P242, E:E242, T:T242", the energy value adder 25 generates, as corrected information, "P:P242, E:E242, T:T242" by using only the energy value E242. Similarly, for example, if the difference between the energy value E252 and the energy value of a gamma ray emitted from a positron-emitting radionuclide is within the predetermined range in the second counted information "P:P252, E:E252, T:T252", the energy value adder 25 generates, as corrected information, "P:P252, E:E252, T:T252" by using only the energy value E252.

As described here, when the energy value adder 25 generates each of the "corrected counted information based on the inner PET detector 14" and the "corrected counted information based on the outer PET detector 15", the simultaneous counted information generator 26 refers to any one of the "corrected counted information based on the inner PET detector 14" and the "corrected counted information based on the inner PET detector 15" and searches for a combination of corrected counted information where the detection time (T) is within a given time window width and the energy value (E) is within a given energy window width and generates simultaneous counted information. Alternatively, the energy value adder 25 may refer to both of "corrected counted information based on the inner PET detector 14" and "corrected counted information based on the inner PET detector 15" and generate simultaneous counted information.

Second Embodiment

Figure 11:
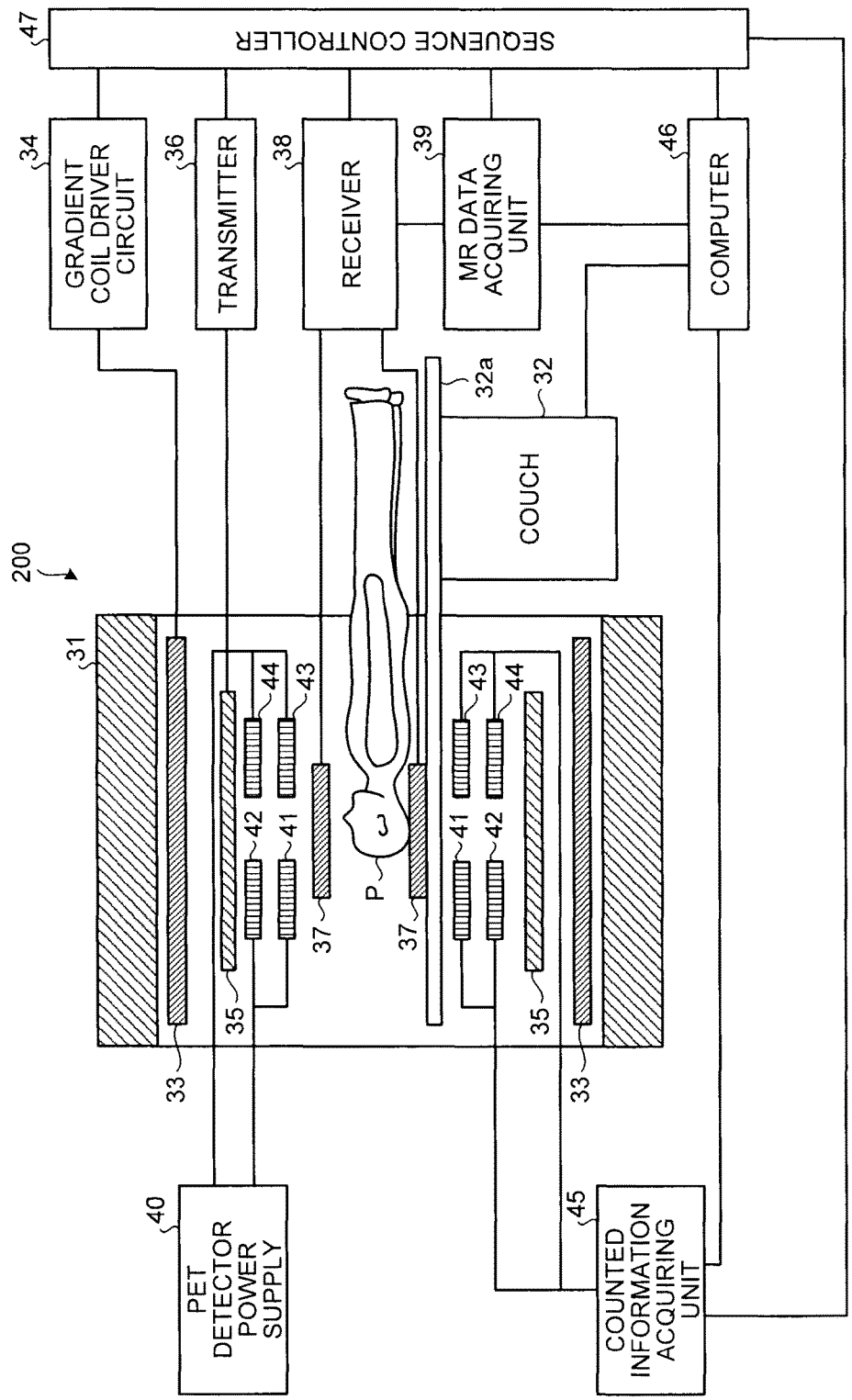
FIG. 11 is a diagram of a configuration of a PET-MRI apparatus according to a second embodiment.

An embodiment of a PET-MRI apparatus will be described as a second embodiment. FIG. 11 is a diagram of a configuration of a PET-MRI apparatus 200 according to the second embodiment. As depicted in FIG. 11, the PET-MRI apparatus 200 includes a static magnetic field magnet 31, a couch 32, a gradient coil 33, a gradient coil driver circuit 34, a transmitting high-frequency coil 35, a transmitter 36, a receiving high-frequency coil 37, a receiver 38, an MR data acquiring unit 39, a PET detector power supply 40, PET detectors 41 to 44, counted information acquiring unit 45, a computer 46, and a sequence controller 47.

The static magnetic field magnet 31 generates a static magnetic field in a cylindrical bore. The bore is formed as an inner wall of an approximately-cylindrical gantry in which the static magnetic field magnet 31 and the gradient coil 33 are housed. The couch 32 includes a couchtop 32a on which a subject P is set. When imaging is performed, the couch 32 moves the subject P into a static magnetic field by moving the couchtop 32a into the bore.

The gradient coil 33 applies, to the subject P, gradient magnetic fields Gx, Gy, and Gz whose magnetic field intensities change linearly in the X, Y, and Z directions. The gradient coil 33 is formed to be approximately cylindrical and is arranged on the inner circumferential side of the static magnetic filed magnet 31. The gradient coil driver circuit 34 drives the gradient coil 33 under the control of the sequence controller 47.

The transmission high-frequency coil 35 applies a high-frequency magnetic field to the subject P, which is set in the static magnetic field, in accordance with a high-frequency pulse transmitted from the transmitter 36. The transmitting high-frequency coil 35 is formed to be approximately cylindrical and arranged on the inner circumferential side of the gradient coil 33. The transmitter 36 transmits a high-frequency pulse to the transmitting high-frequency coil 35 under the control of the sequence controller 47.

The receiving high-frequency coil 37 detects a magnetic resonance signal that is emitted from the subject P in response to application of the high-frequency magnetic field and the gradient magnetic field. For example, the receiving high-frequency coil 37 is a surface coil that is arranged on the surface of the subject P in accordance with a region to be imaged. For example, when the body of the subject P is imaged, two receiving high-frequency coils 37 are arranged above and below the subject. The receiver 38 receives the magnetic resonance signal, which is detected by the receiving high-frequency coil 37, under the control of the sequence controller 47. The receiver 38 transmits the received magnetic resonance signal to the MR data acquiring unit 39.

The MR data acquiring unit 39 acquires the magnetic resonance signal, which is transmitted from the receiver 38, under the control of the sequence controller 47. The MR data acquiring unit 39 amplifies and detects the acquired magnetic resonance signal, performs A/D conversion on the magnetic resonance signal, and then transmits the magnetic resonance signal to the computer 46. The PET detector power supply 40 supplies a power for driving photodetectors, such as photomultiplier tubes, to the PET detectors 41 to 44.

The PET detectors 41 to 44 detect, as counted information, gamma rays that are emitted from positron-emitting radionuclides that are injected into the subject P. The PET detectors 41 to 44 are formed in a ring and are arranged on the inner circumferential side of the transmitting high-frequency coil 35. For example, the PET detectors 41 to 44 are formed by arranging, in a ring, multiple detector modules including scintillators and photodetectors. The scintillator is, for example, a LYSO, LSO, or LGSO. The photodetector is, for example, a semiconductor detector, such as SiPM (silicon photomultiplier) including an APD (avalanche photodiode) device. The PET detectors 41 to 44 transmit the detected counted information to the counted information acquiring unit 45.

Figure 12:
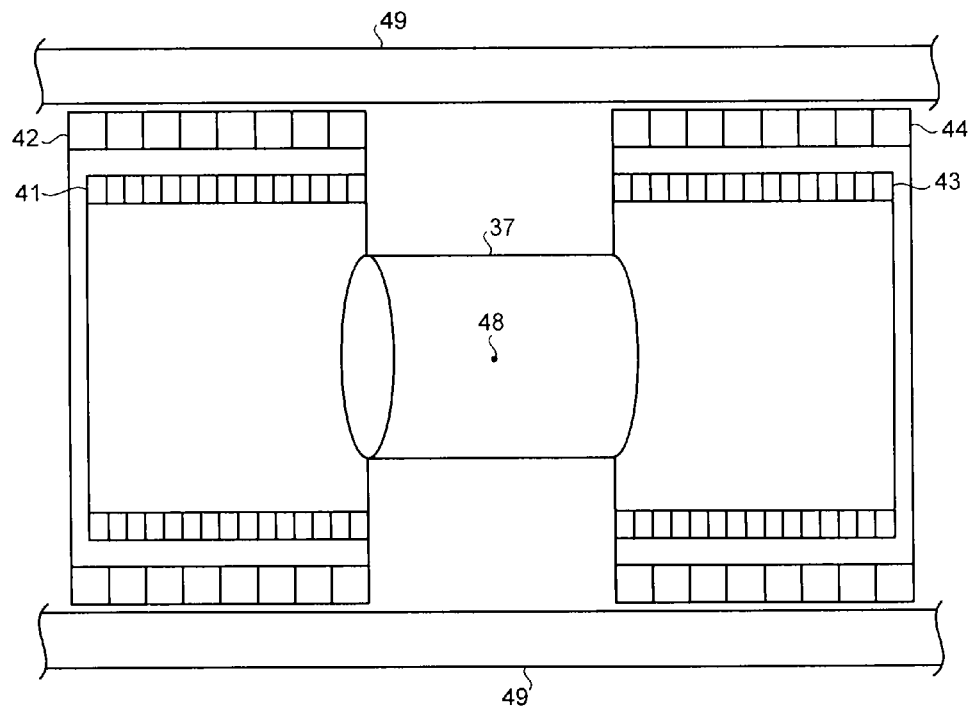
FIG. 12 is a diagram illustrating an arrangement of a PET detector according to the second embodiment.

Arrangement of the PET detectors 41 to 44 will be described in detail here. FIG. 12 is a diagram illustrating an arrangement of the PET detectors 41 to 44 according to the second embodiment. A dot 48 shown in FIG. 12 denotes the magnetic field center of the static magnetic field. The transmitting high-frequency coil 35 is not illustrated in FIG. 12.

As depicted in FIG. 12, the PET detectors 41 to 44 are formed by densely arranging, along a cylindrical surface coaxial with a bore 49, detector modules arranged in the axial direction of the bore 49 and the PET detectors 41 to 44 are arranged in the bore 49. The PET detector 42 is arranged on the outer circumferential side of the PET detector 41. The PET detector 42 detects gamma rays that have passed through the PET detector 41. The PET detector 43 is arranged apart from the PET detector 41 along the axial direction of the bore 49 such that the magnetic field center of the static magnetic field locates between the PET detector 43 and the PET detector 41. The PET detector 44 is provided on the outer circumferential side of the PET detector 43. The PET detector 44 detects gamma rays that have passed through the PET detector 43.

The scintillators of the PET detectors are formed such that, for example, in the case of LYSO, their total thickness is 20 mm or more so as to obtain a gamma ray detection efficiency of a given value or more. For example, an LYSO scintillator of each PET detector is formed such that its total thickness is approximately 22 mm. For example, it is preferable that the thickness of the scintillator of the PET detectors 41 and 43 be approximately 7 to 12 mm. It is also preferable that the thickness of the scintillator of the PET detectors 42 and 44 be approximately 10 to 15 mm. Note that it is preferable that the scintillator of the PET detectors 41 and 43 be thinner than the scintillator of the PET detectors 43 and 44.

As depicted in FIG. 12, also in the second embodiment, the scintillator of the PET detectors 41 and 43 is formed such that its width in the axial direction of the ring is equal to or smaller than the scintillator of the PET detectors 42 and 44.

For example, as depicted in FIG. 12, each scintillator of the PET detectors 41 and 43 is formed such that its width in the axial direction of the ring is smaller than that of the scintillator of the PET detectors 42 and 44 and is formed such that its width is also small in the circumferential direction viewed at the angle as depicted in FIG. 1. In other words, the PET detectors 41 and 43 positioned on the inner side have a higher arrangement area density of scintillators and thus have a smaller pixel size. The PET detectors 42 and 44 positioned on the outer side have a lower arrangement area density of scintillators and thus have a larger pixel size. The material of the scintillators of the PET detectors 41 and 43 and the material of the scintillators of the PET detectors 42 and 44 may be different from each other.

By arranging PET detectors in two layers as described above, the probability of detecting gamma rays can be increased. Regarding the inner PET detectors, by thinning the scintillators, i.e., reducing their width, and reducing the pixel size, the image quality of PET images can be increased. Regarding the outer PET detectors, by increasing the pixel size, the costs of manufacturing the PET detectors can be reduced.

The following refers back to the description of FIG. 11. The counted information acquiring unit 45 acquires, as counted information, information based on the results of counting by the PET detectors 41 to 44. As the counted information acquiring unit 16 of the first embodiment does, the counted information acquiring unit 45 acquires, as counted information, "P: scintillator number", "E: energy value", and "T: detection time" that are associated with "module ID" for uniquely specifying a detector module.

Specifically, the counted information acquiring unit 45 acquires, as first counted information, the detection position, the energy value, and the detection time regarding a gamma ray detected by the PET detector 41. The counted information acquiring unit 45 acquires, as second counted information, the detection position, the energy value, and the detection time regarding a gamma ray detected by the PET detector 42. The counted information acquiring unit 45 acquires, as third counted information, the detection position, the energy value, and the detection time regarding a gamma ray detected by the PET detector 43. The counted information acquiring unit 45 acquires, as fourth counted information, the detection position, the energy value, and the detection time regarding a gamma ray detected by the PET detector 44.

The computer 46 receives various operations from the operator and controls the whole PET-MRI apparatus 200 in accordance with the received operations. For example, the computer 46 reconstructs an MR image on the basis of a magnetic resonance signal transmitted from the MR data acquiring unit 39. The computer 46 reconstructs a PET image on the basis of the counted information acquired by the counted information acquiring unit 45. The sequence controller 47 captures a PET image and an MR image by controlling each unit in accordance with various imaging sequences executed for imaging.

A case is described above where the single computer 46 includes each above-described unit. For example, in consideration of the load of the computer 46, multiple computers may separately include each of the above-described units. For example, two computers may be used, one including functional units related to PET imaging and the other including functional units related to MR imaging.

Figure 13:
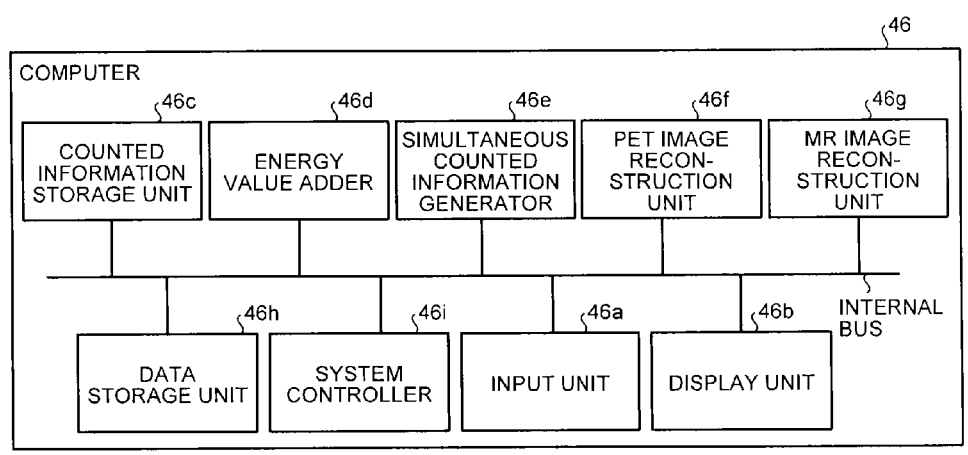
FIG. 13 is a functional block diagram of a configuration of a computer according to the second embodiment.

The computer 46 shown in FIG. 11 will be described in detail below. FIG. 13 is a functional block diagram of a configuration of the computer 46 according to the second embodiment. As depicted in FIG. 13, the computer 46 includes an input unit 46a, a display unit 46b, a counted information storage unit 46c, an energy value adder 46d, a simultaneous counted information generator 46e, a PET image reconstruction unit 46f, an MR image reconstruction unit 46g, a data storage unit 46h, and a system controller 46i. The units of the computer 46 are connected via an internal bus.

The input unit 46a includes a mouse and a keyboard that are used by the operator of the PET-MRI apparatus 200 to input various instructions and various settings and transfers, to the system controller 46i, the information on instructions and settings received from the operator. For example, the input unit 46a receives, from the operator, a reconstruction condition for reconstructing a PET image and a correction condition for image correction. The input unit 46a also receives an imaging condition related to MR image capturing.

The display unit 46b is a monitor referred by the operator and, under the control of the system controller 46i, displays a PET image or an MR image and displays a GUI (graphical user interface) to receive various instructions and various settings from the operator via the input unit 46a.

The counted information storage unit 46c stores first counted information, second counted information, third counted information, and fourth counted information of each detector module that are acquired by the counted information acquiring unit 45. For example, the counted information storage unit 46c stores information similar to the first counted information shown in FIG. 3 as first counted information acquired in accordance with the result of counting performed by a detector module of the PET detector 41. For example, the counted information storage unit 46c stores information similar to the second counted information shown in FIG. 3 as second counted information acquired in accordance with the result of counting performed by a detector module of the PET detector 42.

The counted information storage unit 46c further stores third counted information and fourth counted information. FIG. 14 includes tables of exemplary third counted information stored in the counted information storage unit 46c according to the second embodiment. FIG. 15 includes tables of exemplary fourth counted information stored in the counted information storage unit 46c according to the second embodiment. In FIGS. 14 and 15, "P", "E", and "T" denote "scintillator number", "energy value", and "detection time", respectively.

For example, as shown in FIG. 14, the counted information storage unit 46c stores "P:P311, E:E311, T:T311" and "P:P312, E:E312, T:T312" as third counted information acquired in accordance with the results of counting performed by the detector module of "module ID:D31" of the PET detector 43. The counted information storage unit 46c similarly stores third counted information acquired in accordance with the results of counting performed by the detector modules of "module ID:D32" and "module ID:D33" of the PET detector 43.

For example, as shown in FIG. 15, the counted information storage unit 46c stores "P:P411, E:E411, T:T411" and "P:P412, E:E412, T:4212" as fourth counted information acquired in accordance with the results of counting performed by the detector module of "module ID:D41" of the PET detector 44. The counted information storage unit 46c similarly stores fourth counted information acquired in accordance with the results of counting performed by the detector modules of "module ID:D42" and "module ID:D43" of the PET detector 44.

The following refers back to the description of FIG. 13. On the basis of the counted information stored in the counted information storage unit 46c, the energy value adder 46d generates corrected counted information. As the energy value adder 25 of the first embodiment does, the energy value adder 46d generates corrected counted information on the basis of a time window width contained in the reconstruction condition input by the operator via the input unit 46a.

Specifically, the energy value adder 46d generates first corrected counted information by summing the energy value contained in the first counted information and the energy value contained in the second counted information, which are generated in the same time window. Furthermore, the energy value adder 46*d* generates second corrected counted information by summing the energy value contained in the third counted information and the energy value contained in the fourth counted information, which are generated in the same time window. The energy value adder 46*d* then stores each set of generated corrected counted information in the data storage unit 46*h*.

Specifically, the energy value adder 46*d* searches for a combination of first counted information and second counted information, which is a combination satisfying the vicinity condition, and obtains the energy value of first corrected counted information by summing the energy values. The energy value adder 46*d* similarly searches for a combination of third counted information and fourth counted information, which is a combination satisfying the vicinity condition, and obtains the energy value of second corrected information by summing the energy value. On the basis of each summed energy value of the corrected counted information, the energy value adder 46*d* then makes a comparison with the energy of annihilation radiation emitted from a positron-emitting radionuclide and leaves, as chosen data, only corrected counted information where the difference between the energy values is within a predetermined range.

FIG. 16 is a table of exemplary first corrected counted information generated by the energy value adder 46*d* according to the second embodiment. For example, as shown in FIG. 16, the energy value adder 46*d* generates, as first corrected counted information, "P:P111, E:E111+E211, T:T111" from a combination of the first counted information "P:P111, E:E111, T:T111" shown in FIG. 3 and the second counted information "P:P211, E:E211, T:T211" shown in FIG. 4. Similarly, for example, the energy value adder 46*d* also generates "P:P112, E:E112+E212, T:T112" and "P:P113, E:E113+E213, T:T113" as first corrected counted information.

In addition, for example, the energy value adder 46*d* generates, as first corrected counted information, "P:P151, E:E151+E221, T:T151" from a combination of the first counted information "P:P151, E:E151, T:T151" and the second counted information "P:P221, E:E221, T:T221". Similarly, for example, the energy value adder 46*d* also generates "P:P152, E:E152+E222, T:T152" and "P:P153, E:E153+E223, T:T153" as first corrected counted information.

FIG. 17 is a table of exemplary second corrected counted information generated by the energy value adder 46*d* according to the second embodiment. For example, as shown in FIG. 17, the energy value adder 46*d* generates, as second corrected counted information, "P:P311, E:E311+E411, T:T311" from a combination of the third counted information "P:P311, E:E311, T:T311" shown in FIG. 14 and the fourth counted information "P:P411, E:E411, T:T411" shown in FIG. 15. Similarly, for example, the energy value adder 46*d* generates"P:P313, E:E313+E413, T:T313" and "P:P313, E:E313+E413, T:T313" as second corrected counted information.

Furthermore, for example, the energy value adder 46*d* generates, as second corrected counted information, "P:P351, E:E351+E421, T:T351" from a combination of third counted information "P:P351, E:E351, T:T351" and fourth counted information "P:P421, E:E421, T:T421". Similarly, for example, the energy value adder 46*d* generates "P:P352, E:E352+E422, T:T352" and "P:P353, E:E353+E423, T:T353" as second corrected counted information.

As described above, the energy value adder 46*d* sums the energy value contained in the first counted information and the energy value contained in the second counted information, which are generated in the same time window, so that the energy value of the gamma ray detected by the PET detector 42 is added to the energy value of the gamma ray detected by the PET detector 41. In addition, the energy value adder 46*d* adds the energy value contained in the fourth counted information to the energy value contained in the third counted information, which are generated in the same time window, so that the energy value of the gamma ray detected by the PET detector 44 is added to the energy value of the gamma ray detected by the PET detector 43. Accordingly, the energy values can be compensated for of the gamma rays having passed without having been detected by the PET detectors 41 and 43.

The following refers back to the description of FIG. 13. The simultaneous counted information generator 46*e* generates, as simultaneous counted information, a combination of corrected counted information or of counted information on the approximately simultaneous detection of gamma rays. As the simultaneous counted information generator 26 of the first embodiment does, the simultaneous counted information generator 46*e* generates simultaneous counted information in accordance with the time window width contained in the reconstruction condition, which is input by the operator via the input unit 21, the start of the time window width, and the energy window width.

On the basis of the first corrected counted information and the second corrected counted information, the simultaneous counted information generator 46*e* generates, as simultaneous counted information, a combination of corrected counted information on the approximately simultaneous detection of gamma rays emitted from a positron-emitting radionuclide.

Regarding the corrected counted information obtained as simultaneous counted information, the simultaneous counted information generator 46*e* further generates, as simultaneous counted information, the first counted information and the second counted information of the first correction counted information and the third counted information and the fourth counted information of the second corrected counted information. The simultaneous counted information generator 46*e* also generates, as simultaneous counted information, the counted information of the first corrected counted information and the counted information of the second corrected counted information. Furthermore, the simultaneous counted information generator 46*e* may generate, as simultaneous counted information, a combination of the first corrected counted information and one of the third counted information and the fourth counted information or a combination of the second corrected counted information and one of the first counted information and the second counted information. The simultaneous counted information generator 26 flags the generated simultaneous counted information as projection data (sinogram data) or list mode data on the subject P and stores the simultaneous counted information in the data storage unit 46*h*.

When simultaneous counted information is generated, if the simultaneous counted information is a combination of two sets of counted information of one of the first corrected counted information and the second corrected counted information or a combination of four sets of counted information, the simultaneous counted information generator 46*e* stores the simultaneous counted information in the data storage unit 46*h* in association with high-resolution identifying information representing that the simultaneous counted information is information with which a high-resolution PET image is acquired because data leading to noise is excluded. It is determined which combination is selected in accordance with the processing capacity and processing time of the computer 46.

Furthermore, when simultaneous counted information is generated, if the simultaneous counted information is on gamma rays having passed through an effective imaging area for MR images, the simultaneous counted information generator 46e stores the simultaneous counted information in the data storage unit 46h in association with simultaneous imaging identifying information representing that the simultaneous counted information is information on an area where an MR image and a PET image can be captured simultaneously.

For example, when simultaneous counted information is generated, if the simultaneous counted information is a combination of the first corrected counted information and the fourth counted information or a combination of the third corrected counted information and the second counted information, the simultaneous counted information generator 46e stores the simultaneous counted information in the data storage unit 46h in association with the simultaneous imaging identifying information.

In recent years, a technique referred to as TOF (Time of Flight) is known in which a time difference of detecting a pair of annihilation gamma rays is used to accurately specify the position where the gamma rays are emitted. For example, if the simultaneous counted information is a combination of the first corrected counted information and the fourth counted information or a combination of the third corrected counted information and the second counted information, the simultaneous counted information generator 46e may specify the position where the gamma rays are emitted by using TOF etc., and, if the identified position is within an area between the PET detector 41 and the PET detector 43, the simultaneous imaging identifying information may be associated with simultaneous counted information.

Figures 18, 19:
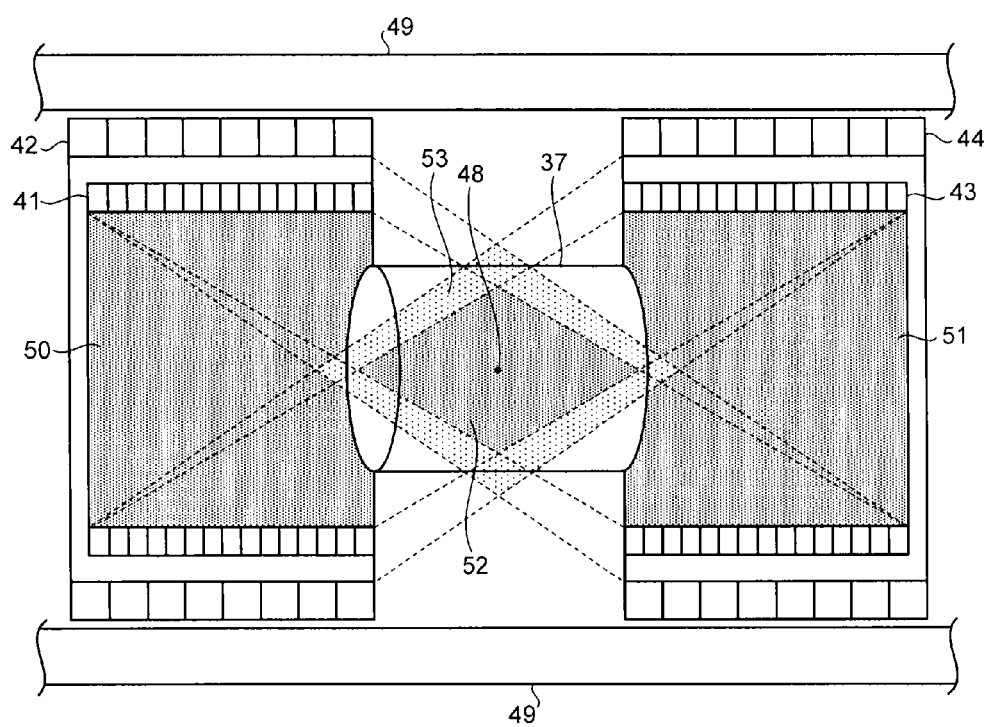
FIG. 18 is a table of exemplary simultaneous counted information generated by a simultaneous counted information generator according to the second embodiment.
FIG. 19 is a diagram of an imaging area for PET images reconstructed by a PET image reconstruction unit according to the second embodiment.

FIG. 18 is a table of exemplary simultaneous counted information generated by the simultaneous counted information generator 46e according to the second embodiment. As shown in FIG. 18, the simultaneous counted information generator 46e generates, as simultaneous counted information, a combination of the first corrected counted information "P:P111, E:E111+E211, T:T111" and "P:P151, E:E151+E221, T:T151" shown in FIG. 16. In this case, the simultaneous counted information generator 46e stores the generated simultaneous counted information in the data storage unit 46h in association with the high-resolution identifying information.

For example, the simultaneous counted information generator 46e generates, as simultaneous counted information, a combination of the second corrected counted information "P:P311, E:E311+E411, T:T311" and "P:P351, E:E351+E421, T:T351" shown in FIG. 17. In this case, the simultaneous counted information generator 46e stores the generated simultaneous counted information in the data storage unit 46h in association with the high-resolution identifying information.

For example, the simultaneous counted information generator 46e generates, as simultaneous counted information, a combination of the first corrected counted information "P:P152, E:E152+E222, T:T152" shown in FIG. 16 and the second corrected counted information "P:P352, E:E352+E422, T:T352" shown in FIG. 17. In this case, the simultaneous counted information generator 46e stores the generated simultaneous counted information in the data storage unit 46h in association with the high-resolution identifying information and the simultaneous imaging identifying information.

For example, the simultaneous counted information generator 46e generates, as simultaneous counted information, a combination of the first corrected counted information "P:P112, E:E112+E212, T:T112" shown in FIG. 16 and the fourth counted information "P:P412, E:E412, T:T412" shown in FIG. 15. In this case, the simultaneous counted information generator 46e stores the generated simultaneous counted information in the data storage unit 46h in association with the simultaneous imaging identifying information.

For example, the simultaneous counted information generator 46e generates, as simultaneous counted information, a combination of the second corrected counted information "P:P312, E:E312+E412, T:T312" shown in FIG. 17 and the second counted information "P:P212, E:E212, T:T212" shown in FIG. 4. In this case, the simultaneous counted information generator 46e stores the generated simultaneous counted information in the data storage unit 46h in association with the simultaneous imaging identifying information.

FIG. 18 shows an example where simultaneous counted information, high-resolution identifying information, and simultaneous imaging identifying information are associated into one set of information. Alternatively, each set of information may be associated with each other and may be stored in different tables.

The following refers back to the description of FIG. 13. The PET image reconstruction unit 46f reads, from the data storage unit 46h, the simultaneous counted information generated by the simultaneous counted information generator 46e and reconstructs a PET image by performing a back projection process on the read projection data. The PET image reconstruction unit 46f stores the reconstructed PET image in the data storage unit 46h.

FIG. 19 is a diagram of an imaging area for PET images reconstructed by the PET image reconstruction unit 46f according to the second embodiment. As depicted in FIG. 19, in the PET-MRI apparatus 200, an effective imaging area 50 surrounded by the inner circumference of the PET detector 41 and an effective imaging area 51 surrounded by the inner circumference of the PET detector 43 are effective imaging areas related to only PET images.

A PET image related to the effective imaging area 50 is reconstructed in accordance with, for example, the simultaneous counted information"P:P111, E:E111+E211, T:T111, P:P121, E:E121+E221, T:T121" shown in FIG. 18. A PET image related to the effective imaging area 50 is reconstructed in accordance with, for example, the simultaneous counted information"P:P311, E:E311+E411, T:T311, P:P321, E:E321+E421, T:T321" shown in FIG. 18.

Regarding the effective imaging areas 50 and 51, the PET detectors 41 and 43 detect gamma rays with a small pixel size and gamma rays having not been detected by the PET detectors 41 and 43 are compensated for by the PET detectors 42 and 43. Accordingly, regarding the effective imaging areas 50 and 51, high-resolution PET images, i.e., PET images with a higher space resolution and higher quantitative performance, can be obtained.

Furthermore, as depicted in FIG. 19, an area 52 that is formed at the center part of the space connecting the inner circumference of the PET detector 41 and the inner circumference of the PET detector 43 and incorporates the magnetic field center 48 serves as the effective imaging area where a PET image and an MR image can be captured simultaneously. The effective imaging area 52 related to PET images and MR images has a shape of cones with their bottom surfaces attached to each other.

A PET image related to the effective imaging area 52 may be reconstructed in accordance with the simultaneous counted information "P:P122, E:E122+E222, T:T122, P:P322, E:E322+E422, T:T322".

Also regarding the effective imaging area 52, the PET detectors 41 and 43 detect gamma rays with a small pixel size and gamma rays having not been detected by the PET detectors 41 and 43 are compensated for by the PET detectors 42 and 44. Accordingly, regarding the effective imaging area 52, PET images with a higher space resolution and higher quantitative performance can be obtained.

As depicted in FIG. 19, an effective imaging area 53 positioned around the effective imaging area 52 related to PET images and MR images is also an effective imaging area where a PET image and an MR image can be captured simultaneously. The effective imaging area 53 is an area where gamma rays are detected approximately simultaneously by a pair of the scintillator of the PET detector 41, which is arranged on the end on the side of the magnetic field center 48, and the scintillator of the PET detector 44, which is arranged on the end on the opening side of the bore 49, or a pair of a scintillator of the PET detector 43, which is arranged on the end on the side of the magnetic field center 48, and a scintillator of the PET detector 42, which is arranged on the end on the opening side of the bore 49.

A PET image related to the effective imaging area 53 may be reconstructed in accordance with the simultaneous counted information "P:P112, E:E112+E212, T:T112, P:P412, E:E412, T:T412" or "P:P312, E:E312+E412, T:T312, P:P212, E:E212, T:T212".

Regarding the effective imaging area 53, one of the PET detectors that have detected gamma rays is an outer PET detector with a pixel size larger than that of the inner PET detector. Thus, although the space resolution is lower than those of the effective imaging areas 50 to 52, a PET image of the effective imaging area 53 can be obtained. Accordingly, the area where a PET image and an MR image can be simultaneously captured can be broadened.

The following refers back to the description of FIG. 13. The MR image reconstruction unit 46g reconstructs an MR image on the basis of the magnetic resonance signals acquired by the MR data acquiring unit 39. For example, the MR image reconstruction unit 46g arranges the magnetic resonance signals, which are acquired by the MR data acquiring unit 39, in a k space and generates k space data. The MR image reconstruction unit 46g generates an internal MR image of the subject P by performing a post process, i.e., a reconstruction process such as the Fourier transform, on the generated k space data.

The data storage unit 46h stores various types of information and various programs. For example, the data storage unit 46h stores each set of corrected counted information, which is generated by the energy value adder 46d. The data storage unit 46h stores the simultaneous counted information, high-resolution identifying information, and simultaneous imaging identifying information that are generated by the simultaneous counted information generator 26. The data storage unit 46h also stores the PET images reconstructed by the PET image reconstruction unit 46f and the MR images reconstructed by the MR image reconstruction unit 46g.

The system controller 46i controls the whole PET-MRI apparatus 200 by controlling operations of each unit of the PET-MRI apparatus 200 according to instructions from the operator. For example, the system controller 46i receives a reconstruction condition for reconstructing a PET image, a correction condition for image correction, and an imaging condition regarding MR image capturing. The system controller 46i controls the sequence controller 47 in accordance with the received various conditions. The system controller 46i controls the display unit 466 to display the PET image or the MR image stored in the data storage unit 46h.

Figure 20:
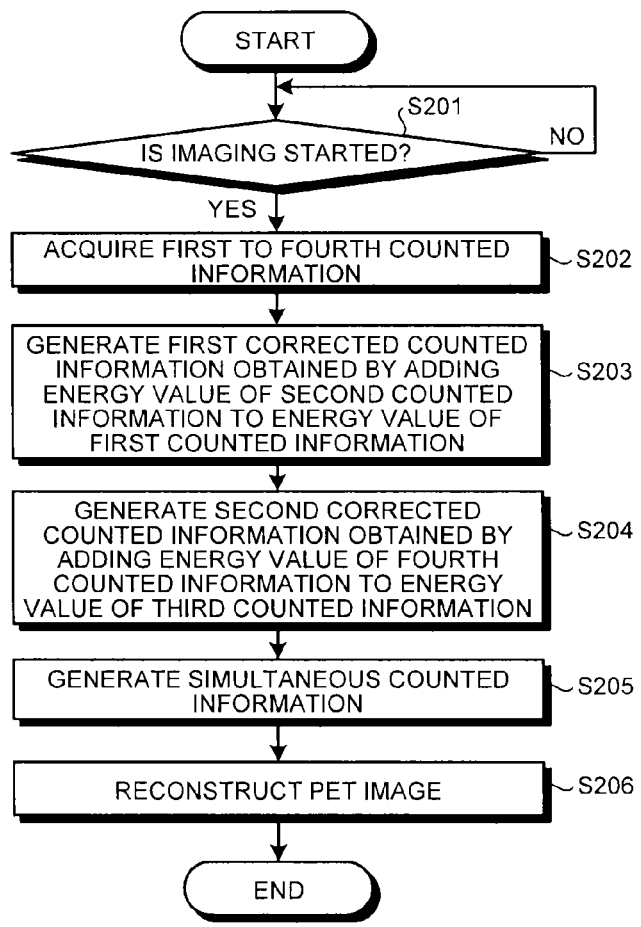
FIG. 20 is a flowchart of the flow of PET image capturing performed by the PET-MRI apparatus according to the second embodiment.

The flow of PET image capturing performed by the PET-MRI apparatus 200 according to the second embodiment will be described here. FIG. 20 is a flowchart of the flow of PET image capturing performed by the PET-MRI apparatus 200 according to the second embodiment. As shown in FIG. 20, once the PET-MRI apparatus 200, after moving the subject P into the bore, receives a PET-image capturing start instruction from the operator via the input unit 46a (YES at step S201), the PET-MRI apparatus 200 performs the following process.

First, the counted information acquiring unit 45 acquires, as first to fourth counted information, the detection positions, the energy values, and the detection time regarding gamma rays detected by the PET detectors 41 to 44 (step S202).

Subsequently, on the basis of the detection time contained in the first counted information and the detection time contained in the second counted information, the energy value adder 46d generates first corrected counted information by adding the energy value contained in the second counted information to the energy value contained in the first counted information (step S203). Furthermore, on the basis of the detection time contained in the third counted information and the detection time contained in the fourth counted information, the energy value adder 46d generates second corrected counted information by adding the energy value contained in the fourth counted information to the energy value contained in the third counted information (step S204).

Subsequently, the simultaneous counted information generator 46e generates, as simultaneous counted information, a combination of the first corrected counted information, a combination of the second corrected counted information, a combination of the first corrected counted information and the second corrected counted information, a combination of the first corrected counted information and the fourth corrected counted information, and a combination of the third corrected counted information and the second counted information, each of which is a combination on the simultaneous detection of gamma rays (step S205). The time information used here is the time information of the used PET detector 41 or 43.

The PET image reconstruction unit 46f reconstructs a PET image by using, as projection data, the simultaneous counted information generated by the simultaneous counted information generator 46e (step S206). The captured PET image is displayed on, for example, the display unit of the computer 46.

Figure 21:
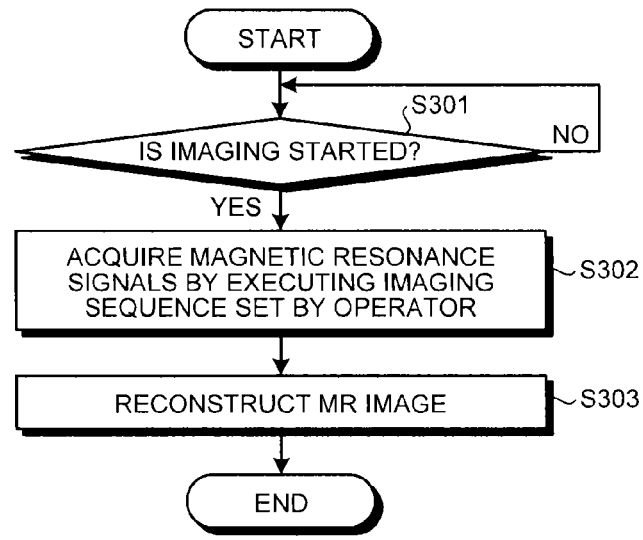
FIG. 21 is a flowchart of the flow of MR image capturing performed by the PET-MRI apparatus according to the second embodiment.

The flow of MR image capturing performed by the PET-MRI apparatus 200 according to the second embodiment will be described here. FIG. 21 is a flowchart of the flow of PET image capturing performed by the PET-MRI apparatus 200 according to the second embodiment. As shown in FIG. 21, once the PET-MRI apparatus 200, after moving the subject P into the bore, receives a MR-image capturing start instruction from the operator via the input unit 46a (YES at step S301), the PET-MRI apparatus 200 performs the following process.

First, by controlling the gradient coil 33, the transmitter 36, the receiver 38, and the MR data acquiring unit 39, the sequence controller 47 executes the imaging sequence set by the operator and acquires magnetic resonance signals (step S302).

The computer 46 reconstructs an MR image on the basis of the acquired magnetic resonance signals (step S303). The captured MR image is displayed on the display unit of the computer 46.

The PET image capturing shown in FIG. 20 and the MR image capturing shown in FIG. 21 may be perfumed independently or in parallel.

As described above, the PET-MRI apparatus 200 according to the second embodiment includes the static magnetic field magnet 31, the receiving high-frequency coil 37, the MR image reconstruction unit 46g, the PET detectors 41 to 44, the counted information acquiring unit 45, the energy value adder 46d, the simultaneous counted information generator 46e, and the PET image reconstruction unit 46f. The static magnetic field magnet 31 generates a static magnetic field in the cylindrical bore. The receiving high-frequency coil 37 detects a magnetic resonance signal emitted from the subject P, which is put in the static magnetic field, in response to application of a high-frequency pulse and a gradient magnetic field to the subject P. The MR image reconstruction unit 46g reconstructs an MR image on the basis of the magnetic resonance signals detected by the receiving high-frequency coil 37. The PET detectors 41 and 43 detect gamma rays emitted from positron-emitting radionuclides that are injected into the subject P. The PET detectors 42 and 44 are provided on the outer circumferential side of the PET detectors 41 and 43 and detect gamma rays that have passed through the PET detectors 41 and 43. The counted information acquiring unit 45 acquires, as first counted information, the detection positions, the energy values, and the detection time regarding gamma rays detected by the PET detectors 41 and 43 and acquires, as second counted information, the detection positions, the energy values, and the detection time regarding gamma rays detected by the PET detectors 42 and 44. On the basis of the detection time contained in the first counted information and the detection time contained in the second counted information, the counted information acquiring unit 45 generates corrected counted information by adding the energy value contained in the second counted information to the energy value contained in the first counted information. On the basis of the corrected counted information generated by the energy value adder 46d, the simultaneous counted information generator 46e generates, as simultaneous counted information, a combination of corrected counted information on the simultaneous detection of gamma rays emitted from a positron-emitting radionuclide. The PET image reconstruction unit 46f reconstructs a PET image by using the simultaneous counted information, which is generated by the simultaneous counted information generator 46e, as projection data. In other words, in the second embodiment, the inner PET detectors 41 and 43 ensure the space resolution and of PET images and the outer PET detectors 42 and 44 ensure the gamma ray detection efficiency. Accordingly, according to the second embodiment, the space solution and quantitative performance of imaged PET images can be improved.

In the second embodiment, the PET detector 41 and the PET detector 43 are arranged apart from each other along the axial direction of the bore such that the magnetic field center of the static magnetic field is between the PET detector 43 and the PET detector 41. The counted information acquiring unit 45 acquires, as third counted information, the detection position, the energy value, and the detection time regarding a gamma ray detected by the PET detector 43 and acquires, as fourth counted information, the detection position, the energy value, and the detection time regarding a gamma ray detected by the PET detector 44. The energy value adder 46d generates first corrected counted information by adding the energy value contained in the second counted information to the energy value contained in the first counted information and generates second corrected counted information by adding the energy value contained in the fourth counted information to the energy value contained in the third counted information. On the basis of the first corrected counted information and the second corrected counted information, the simultaneous counted information generator 46e generates, as simultaneous counted information, a combination of first corrected counted information on simultaneous detection of gamma rays, a combination of second corrected counted information on simultaneous detection of gamma rays, and a combination of first corrected counted information and second corrected counted information on simultaneous detection of gamma rays. Thus, according to the second embodiment, the PET detectors 41 and 43 are arranged away from the vicinity of the magnetic field center serving as the imaging effective area for MR images. Accordingly, according to the second embodiment, image quality degradation of MR images due to the effects of the PET detectors can be reduced.

In the second embodiment, the counted information acquiring unit 45 further acquires, as second counted information, the detection position regarding a gamma ray detected by the PET detector 42 and further acquires, as fourth counted information, the detection position regarding a gamma ray detected by the PET detector 44. The simultaneous counted information generator 46e further generates, as simultaneous counted information, a combination of first corrected counted information and fourth counted information on the simultaneous detection of gamma rays and a combination of third corrected counted information and second counted information on the simultaneous detection of gamma rays. Accordingly, according to the second embodiment, a PET image and an MR image can be captured simultaneously in a broader area.

In the second embodiment, when the simultaneous counted information generator 46e generates simultaneous counted information, if the simultaneous counted information is on a gamma ray that has passed through the effective imaging area for MR images, the simultaneous counted information generator 46e stores the simultaneous counted information in the data storage unit 46h in association with simultaneous imaging identifying information representing that the simultaneous counted information is information on an area where an MR image and a PET image can be captured simultaneously in the area. Thus, according to the second embodiment, it is easily determined whether the simultaneous counted information is on the effective imaging area for MR images. Accordingly, for example, a radiologist etc. can be informed of whether a clinical PET image is captured simultaneously with an MR image or whether a clinical MR image is captured simultaneously with a PET image.

In the second embodiment, a case is described where the energy value adder 46d adds the energy value contained in the second counted information to the energy value contained in the first counted information and adds the energy value contained in the fourth counted information to the energy value contained in the third counted information and thus the outer PET detectors 42 and 44 compensate for the energy values of gamma rays that have not been detected by the inner PET detectors 41 and 43.

However, for example, as described in the first embodiment, the inner PET detectors 41 and 43 may compensate for the energy values of gamma rays that have not been detected by the outer PET detectors 42 and 44.

In this case, as is the case of the first embodiment, the energy value adder 46d searches for the PET detector 42 that satisfies the vicinity condition on the inner PET detector 41 and the energy value adder 46d generates "first corrected counted information based on the inner PET detector 41". The energy value adder 46d searches for the PET detector 41 that satisfies the vicinity condition on the outer PET detector 42 and the energy value adder 25 generates "first corrected counted information based on the outer PET detector 42" (see FIG. 8). Similarly, the energy value adder 46d generates "second corrected counted information based on the inner PET detector 43" and "second corrected counted information based on the outer PET detector 44".

Here, for example, when the difference between the energy value of the gamma ray emitted from the positron-emitting radionuclide and only one of the energy value of the first counted information and the energy value of the second counted information is within the given value, the energy value adder 46d may generate first corrected counted information by using only one of the energy value of the first counted information and the energy value of the second counted information (see FIGS. 9 and 10). Similarly, when the difference between the energy value of the gamma ray emitted from the positron-emitting radionuclide and only one of the energy value of the third counted information and the energy value of the fourth counted information is within the given value, the energy value adder 46d may generate second corrected counted information by using only one of the energy value of the third counted information and the energy value of the fourth counted information.

As described above, when the energy value adder 46d generates "first corrected counted information based on the inner PET detector 41", "first corrected counted information based on the outer PET detector 42", "second corrected counted information based on the inner PET detector 43", and "second corrected counted information based on the outer PET detector 44", the simultaneous counted information generator 46e may generate simultaneous counted information by using the "first corrected counted information based on the inner PET detector 41" and the "second corrected counted information based on the inner PET detector 43" and generate simultaneous counted information by using the "first corrected counted information based on the outer PET detector 42" and the "second corrected counted information based on the outer PET detector 44". The energy value adder 46d may generate simultaneous counted information with reference to all the corrected counted information.

Third Embodiment

A third embodiment will be described here. In the third embodiment, a case will be described where, in the PET-MRI apparatus 200 described in the second embodiment, imaging is repeated while gradually moving the couchtop 32a, on which the subject P is put, into the bore 49 in the axial direction. Such imaging method is referred to as step-and-shoot.

Figure 22:
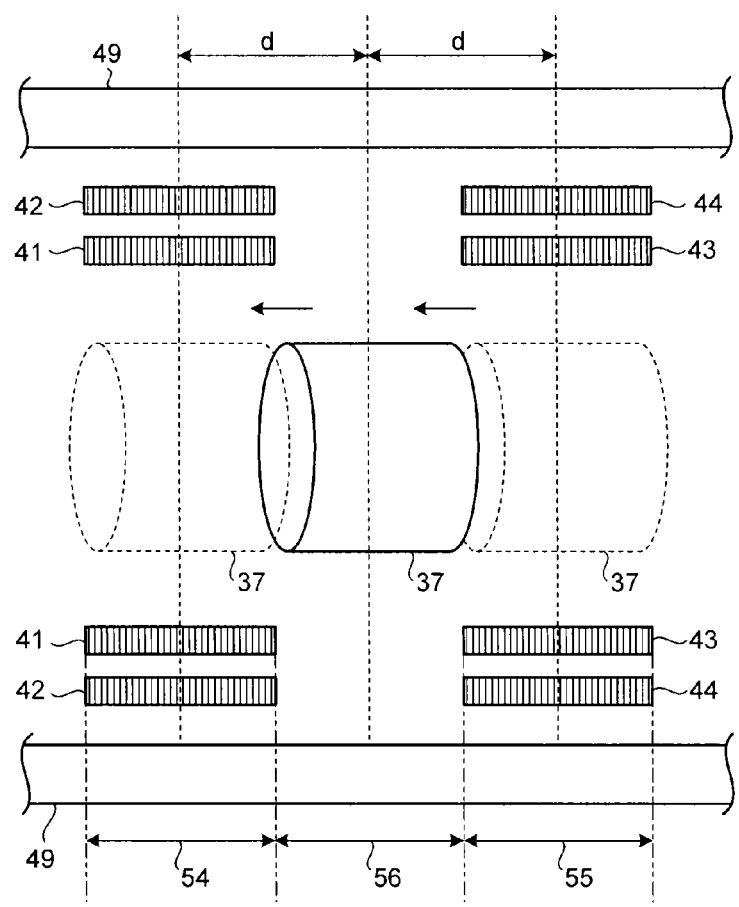
FIG. 22 is a diagram illustrating step-and-shoot according to a third embodiment.

FIG. 22 is a diagram illustrating step-and-shoot according to the third embodiment. In the step-and-shoot, the couch 32 moves the subject P along the axial direction of the bore 49 by moving the couchtop 32a. The computer 46 controls the couch 32 such that the region to be imaged of the subject P gradually moves sequentially to an approximately center position of the PET detector 43, an approximately canter position of an area between the PET detector 41 and the PET detector 43, and an approximately center position of the PET detector 41.

Accordingly, as depicted in FIG. 22, the receiving high-frequency coil 37, which is attached to the imaging position of the subject P, gradually moves. Specifically, the receiving high-frequency coil 37 gradually moves, in the axial direction of the bore 49, a distance d that is half of the interval between the center of the PET detector 41 and the center of the PET detector 43. As a result, the region to be imaged is moved in the axial direction of the bore 49 sequentially to an area 55 where only a PET image can be captured, an area 56 where a PET image and a PET image can be captured simultaneously, and an area 54 where only a PET image can be captured.

For example, when the region to be imaged is moved to the approximately center position of the PET detector 41 or the approximately center position of the PET detector 43, the computer 46 controls the PET-MRI apparatus 200 so as to capture a PET image. When the region to be imaged is moved to the approximately center position of the area between the PET detector 41 and the PET detector 43, the computer 46 controls the PET-MRI apparatus 200 to capture a PET image and/or an MR image. Accordingly, it is possible to sequentially capture a PET image and capture an MR image and/or a PET image while gradually moving the region to be imaged.

In the first to third embodiments, a case is described where detection positions are acquired where not only gamma rays detected by the inner PET detectors but gamma rays detected by the outer PET detectors are acquired. However, for example, the outer PET detector does not need to acquire any gamma ray detection position. In such a case, because it is unnecessary to arrange multiple scintillators in the axial direction of the bore, costs of PET detectors can be further reduced.

Furthermore, in the first to third embodiments, a case is described where PET detectors are arranged in two layers. However, embodiments of the PET device, PET-MRI apparatus, and image processing method are not limited to them. For example, PET detectors may be arranged in three layers or more. In other words, an additional PET detector is arranged on the outer side of the outer PET detector. Accordingly, gamma rays that have not detected by the inner PET detectors can be compensated more accurately.

In the second and third embodiments, a case is described where two pairs of PET detectors arranged in two layers are arranged. However, embodiments of the PET-MRI apparatus are not limited to this. For example, three or more pairs of PET detectors arranged in two layers may be arranged along the axial direction of the bore. In other words, even if three or more pairs of PET detectors 13a and 13b are arranged, a PET image and an MR image can be captured simultaneously in areas between each PET detector.

In the first embodiment, a case is described where a pair of PET detectors arranged in two layers is arranged. However, embodiments of the PET device are not limited to this. For example, as is the case of the PET-MRI apparatus 200 described in the second and third embodiments, multiple pairs of PET detectors arranged in two layers may be arranged. In such a case, for example, the PET device 100 according to the first embodiment further includes a ring-shaped third PET detector that is arranged apart from the PET detector 14 along the axial direction of the PET detector 14 and detects gamma rays emitted from positron-emitting radionuclides injected into the subject P. The PET device 100 is provided on the outer circumferential side of the third PET detector and further includes a ring-shaped fourth PET detector that detects gamma rays that have passed through the third PET detector. As the counted information acquiring unit 45 described in the second embodiment does, the counted information acquiring unit 16 acquires the detection position, the energy value, and the detection time regarding a gamma ray detected by each PET detector. As the energy value adder 25 described in the second embodiment does, the energy value adder 46d generates corrected counted information by adding the energy value detected by the outer PET detector to the energy value detected by the inner PET detector. As the simultaneous counted information generator 26 described in the second embodiment does, the simultaneous counted information generator 46e generates, as simultaneous counted information, a combination of corrected counted information on simultaneous detection of gamma rays.

As described above, according to the first to third embodiments, a PET device, a PET-MRI apparatus, and an image processing method can be achieved that can improve the image quality of captured PET images.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A positron emission computed tomography (PET) device comprising:
    a first PET detector having a ring shape and having a first radius, the first PET detector including a plurality of first scintillators arranged in a ring shape and configured to detect a plurality of gamma rays emitted from positron-emitting radionuclides injected into a subject, the ring shape of the plurality of first scintillators defining an outer circumferential side;
    a second PET detector having a ring shape and having a second radius greater than the first radius, the second PET detector including a plurality of second scintillators arranged in a ring shape and configured to detect at least one gamma ray of the plurality of gamma rays that has passed through the first scintillators, the ring shape of the plurality of second scintillators defining an inner circumferential side, wherein the first PET detector and the second PET detector are concentric, wherein the outer circumferential side of the first plurality of scintillators faces the inner circumferential side of the second plurality of scintillators, wherein a pixel size of the second scintillators is larger than a pixel size of the first scintillators, wherein a length of the second PET detector in its axial direction is longer than that of the first PET detector; and
    a processor in communication with the plurality of first scintillators and the plurality of second scintillators, the processor configured to
    acquire first counted information including a detection position, an energy value, and a detection time regarding the plurality of gamma rays detected by one of the first scintillators and acquire second counted information including a detection position, an energy value, and a detection time regarding the at least one gamma ray detected by one of the second scintillators;
    when a difference between the detection time comprised by the first counted information and the detection time comprised by the second counted information is within a time window width that is selected to determine whether the first counted information and the second counted information correspond to said at least one gamma ray, generate corrected counted information for said at least one gamma ray by adding the energy value comprised by the second counted information for said at least one gamma ray to the energy value comprised by the first counted information for said at least one gamma ray;
    based on the corrected counted information, generate simultaneous counted information based on a combination of the corrected counted information on simultaneous detection of the plurality of gamma rays emitted from the positron-emitting radionuclides; and
    reconstruct a PET image in accordance with the simultaneous counted information.

2. The PET device according to claim 1, wherein the first scintillators have a first thickness, and the second scintillators have a second thickness that is greater than the first thickness.

3. The PET device according to claim 1, further comprising:
    a third PET detector having a ring shape and having a third radius, the third PET detector including a plurality of third scintillators arranged in a ring shape defining an outer circumferential side, arranged apart from the first scintillators along the axial direction of the first scintillators, and configured to detect a plurality of second gamma rays emitted from the positron-emitting radionuclides injected into the subject; and
    a fourth PET detector having a ring shape and having a fourth radius greater third radius, the fourth PET detector including a plurality of fourth scintillators arranged in a ring shape and configured to detect at least one second gamma ray of the plurality of second gamma rays that has passed through the third scintillators, the ring shape of the plurality of fourth scintillators defining an inner circumferential side, wherein the third PET detector and the fourth PET detector are concentric, wherein the outer circumferential side of the third plurality of scintillators faces the inner circumferential side of the fourth plurality of scintillators, and wherein the third PET detector and the fourth PET detector are axially spaced from the first PET detector and the second PET detector,
    wherein
    the processor acquires third counted information including a detection position, an energy value, and a detection time regarding the plurality of second gamma rays detected by one of the third scintillators and acquires fourth counted information including a detection position, an energy value, and a detection time regarding the at least one second gamma ray detected by one of the fourth scintillators and determines the first counted information and the second counted information for said at least one gamma ray, and the third counted information and the fourth counted information for said at least one second gamma ray,
    the processor generates said corrected counted information as first corrected counted information for said at least one gamma ray by adding the energy value comprised by the second counted information for said at least one gamma ray to the energy value comprised by the first counted information for said at least one gamma ray and generates second corrected counted information for said at least one second gamma ray by adding the energy value comprised by the fourth counted information for said at least one second gamma ray to the energy value comprised by the third counted information for said at least one second gamma ray, and based on the first corrected counted information and the second corrected counted information, the processor generates the simultaneous counted information based on a combination of the first corrected counted information on the simultaneous detection of the plurality of gamma rays emitted from the positron-emitting radionuclides, a combination of the second corrected counted information on simultaneous detection of the plurality of second gamma rays emitted from the positron-emitting radionuclides, and a combination of the first corrected counted information and the second corrected counted information on simultaneous detection of the plurality of gamma rays and the plurality of second gamma rays emitted from the positron-emitting radionuclides, each of the combinations comprising a sum of corresponding ones of the energy values.

4. The PET device according to claim 1, wherein the processor is configured to compare an energy value comprised by the generated corrected counted information with an energy value of the plurality of gamma rays emitted from the positron-emitting radionuclides and chooses the corrected counted information where a difference between the energy value comprised by the generated counted information and the energy value of the plurality of gamma rays emitted from the positron-emitting radionuclides is within a predetermined range, and the processor is configured such that, based on the corrected counted information which is chosen, the processor generates the simultaneous counted information.

5. A positron emission computed tomography-magnetic resonance imaging (PET-MRI) apparatus comprising:

a static magnetic field magnet configured to generate a static magnetic field in a cylindrical bore;

a high-frequency coil configured to detect a magnetic resonance signal emitted from a subject placed in the static magnetic field, in response to application of a high-frequency pulse and a gradient magnetic field to the subject;

a first PET detector having a ring shape and having a first radius, the first PET detector including a plurality of first scintillators arranged in a ring shape and configured to detect a plurality of gamma rays that are emitted from positron-emitting radionuclides that are injected into the subject, the ring shape of the plurality of first scintillators defining an outer circumferential side;

a second PET detector having a ring shape and having a second radius greater than the first radius, the second PET detector including a plurality of second scintillators arranged in a ring shape and configured to detect at least one gamma ray of the plurality of gamma rays that has passed through the first scintillators, the ring shape of the plurality of second scintillators defining an inner circumferential side, wherein the first PET detector and the second PET detector are concentric, wherein the outer circumferential side of the first plurality of scintillators faces the inner circumferential side of the second scintillators is larger than a pixel size of the first scintillators, wherein a length of the second PET detector in its axial direction is longer than that of the first PET detector; and a processor in communication with the high-frequency coil, the plurality of first scintillators, and the plurality of second scintillators, the processor configured to reconstruct an MR image based on the magnetic resonance signal detected by the high-frequency coil;

acquire first counted information including a detection position, an energy value, and a detection time regarding the plurality of gamma rays detected by one of the first scintillators and acquire second counted information including a detection position, an energy value, and a detection time regarding the at least one gamma ray detected by one of the second scintillators;

when a difference between the detection time comprised by the first counted information and the detection time comprised by the second counted information is within a time window width that is selected to determine whether the first counted information and the second counted information correspond to said at least one gamma ray, generate corrected counted information for said at least one gamma ray by adding the energy value comprised by the second counted information for said at least one gamma ray to the energy value comprised by the first counted information for said at least one gamma ray;

based on the corrected counted information, generate simultaneous counted information based on a combination of the corrected counted information on simultaneous detection of the plurality of gamma rays emitted from the positron-emitting radionuclides; and reconstruct a PET image in accordance with the simultaneous counted information.

6. The PET-MRI apparatus according to claim 5, wherein the first scintillators have a first thickness, and the second scintillators have a second thickness that is greater than the first thickness.

7. The PET-MRI apparatus according to claim 5, further comprising:

a third PET detector having a ring shape and having a third radius, the third PET detector including a plurality of third scintillators arranged in a ring shape to define an outer circumferential side and arranged apart from the first scintillators along an axial direction of the cylindrical bore such that a magnetic field center of the static magnetic field is between the first scintillators and the third scintillators; and a fourth PET detector having a ring shape and having a fourth radius greater than the third radius, the fourth PET detector including a plurality of fourth scintillators arranged in a ring shape and configured to detect at least one second gamma ray of the plurality of second gamma rays that has passed through the third scintillators, the ring shape of the plurality of fourth scintillators defining an inner circumferential side, wherein the third PET detector and the fourth PET detector are concentric, wherein the outer circumferential side of the third plurality of scintillators faces the inner circumferential side of the fourth plurality of scintillators, and wherein the third PET detector and the fourth PET detector are axially spaced from the first PET detector and the second PET detector, wherein the processor acquires third counted information including a detection position, an energy value, and a detection time regarding the plurality of second gamma rays detected by one of the third scintillators and acquires fourth counted information including a detection position, an energy value, and a detection time regarding the at least one second gamma ray detected by one of the fourth scintillators and determines the first counted information and the second counted information for a said at least one gamma ray, and the third counted information and the fourth counted information for said at least one second gamma ray, the processor generates said corrected counted information as first corrected counted information for said at least one gamma ray by adding the energy value comprised by the second counted information for said at least one gamma ray to the energy value comprised by the first counted information for said at least one gamma ray and generates second corrected counted information for said at least one second gamma ray by adding the energy value comprised by the fourth counted information for said at least one second gamma ray to the energy value comprised by the third counted information for said at least one second gamma ray, and based on the first corrected counted information and the second corrected counted information, the processor generates simultaneous counted information based on a combination of the first corrected counted information on the simultaneous detection of the plurality of gamma rays emitted from the positron-emitting radionuclides, a combination of the second corrected counted information on simultaneous detection of the plurality of second gamma rays emitted from the positron-emitting radionuclides, and a combination of the first corrected counted information and the second corrected counted information on simultaneous detection of the plurality of gamma rays and plurality of second gamma rays emitted from the positron-emitting radionuclides, each of the combinations comprising a sum of corresponding ones of the energy values.

8. The PET-MRI apparatus according to claim 7, wherein the processor is configured such that the processor further generates the simultaneous counted information to further comprise a combination of the first corrected counted information and the fourth counted information on the simultaneous detection of the plurality of gamma rays and the plurality of second gamma rays and a combination of the third counted information and the second counted information on the simultaneous detection of the plurality of gamma rays and the plurality of second gamma rays.

9. The PET-MRI apparatus according to claim 7, further comprising:
a driver configured to move the subject along the axial direction of the cylindrical bore; and
wherein the processor is configured to control the driver such that the driver moves a region to be imaged of the subject to an approximate center of any one of the plurality of first scintillators and the plurality of third scintillators and an approximately center position of an area between the first scintillators and the third scintillators, perform control such that the PET image is captured when the region to be imaged is moved to an approximately center position of the first scintillators or the third scintillators, and control the MRI image and/or the PET image to be captured when the region to be imaged is moved to the approximately center position of the area between the first scintillators and the third scintillators.

10. The PET-MRI apparatus according to claim 5, wherein, upon generation of the simultaneous counted information, when the simultaneous counted information is on one of the plurality of gamma rays that has passed through an effective imaging area for MR images, the processor stores the simultaneous counted information in association with simultaneous imaging identifying information representing that the simultaneous counted information is information on an area where the MR image and the PET image can be captured simultaneously.

11. The PET-MRI apparatus according to claim 5, wherein the processor is configured such that
the processor compares an energy value comprised by the generated corrected counted information with the energy value of the plurality of gamma rays emitted from the positron-emitting radionuclides and chooses corrected counted information where a difference between the energy value comprised by the generated corrected counted information and the energy value of the plurality of gamma rays emitted from the positron-emitting radionuclides is within a predetermined range, and
based on the corrected counted information, which is chosen by the processor, the processor generates the simultaneous counted information.

12. The PET-MRI apparatus according to claim 5, wherein each of the first scintillators is formed such that its length in an axial direction of the ring shape is smaller than that of each of the second scintillators.

13. An image processing method comprising:
detecting, by a first PET detector having a ring shape and having a first radius, the first PET detector including a plurality of first scintillators arranged in a ring shape to define an outer circumferential side, a plurality of gamma rays that are emitted from positron-emitting radionuclides that are injected into a subject;
detecting, by a second PET detector having a ring shape and having a second radius greater than the first radius, the second PET detector including a plurality of second scintillators arranged in a ring shape, at least one gamma ray of the plurality of gamma rays that has passed through the first scintillators, the ring shape of the plurality of second scintillators defining an inner circumferential side, wherein the first PET detector and the second PET detector are concentric, wherein the outer circumferential side of the first plurality of scintillators faces the inner circumferential side of the second plurality of scintillators, wherein a pixel size of the second scintillators is larger than a pixel size of the first scintillators, and wherein a length of the second PET detector in its axial direction is longer than that of the first PET detector;
acquiring first counted information including a detection position, an energy value, and a detection time regarding the plurality of gamma rays detected by one of the first scintillators and acquiring second counted information including a detection position, an energy value, and a detection time regarding the at least one gamma ray detected by one of the second scintillators;
when a difference between the detection time comprised by the first counted information and the detection time comprised by the second counted information is within a time window width that is selected to determine whether the first counted information and the second counted information correspond to said at least one gamma ray, generating corrected counted information for said at least one gamma ray by adding the energy value contained in the second counted information for said at least one gamma ray to the energy value contained in the first counted information for said at least one gamma ray;

generating, as simultaneous counted information, a combination of the corrected counted information on simultaneous detection of the plurality of gamma rays emitted from the positron-emitting radionuclides, based on the corrected counted information; and reconstructing a PET image in accordance with the simultaneous counted information.

14. The PET device according to claim 1, wherein each of the first scintillators is formed such that its length in an axial direction of the ring shape is smaller than that of each of the second scintillators.

* * * * *